US012266096B2

(12) United States Patent
Kapur et al.

(10) Patent No.: US 12,266,096 B2
(45) Date of Patent: Apr. 1, 2025

(54) SYSTEMS AND METHODS FOR PROCESSING IMAGES OF SLIDES TO INFER BIOMARKERS

(71) Applicant: PAIGE.AI, Inc., New York, NY (US)

(72) Inventors: Supriya Kapur, New York, NY (US); Ran Godrich, New York, NY (US); Christopher Kanan, Rochester, NY (US); Thomas Fuchs, New York, NY (US); Leo Grady, Darien, CT (US)

(73) Assignee: Paige.AI, Inc., New York, NY (US)

( * ) Notice: Subject to any disclaimer, the term of this patent is extended or adjusted under 35 U.S.C. 154(b) by 424 days.

(21) Appl. No.: 17/016,048

(22) Filed: Sep. 9, 2020

(65) Prior Publication Data
US 2021/0073986 A1  Mar. 11, 2021

Related U.S. Application Data

(60) Provisional application No. 62/897,734, filed on Sep. 9, 2019.

(51) Int. Cl.
*G06T 7/00* (2017.01)
*G06F 18/214* (2023.01)
(Continued)

(52) U.S. Cl.
CPC .......... *G06T 7/0012* (2013.01); *G06F 18/214* (2023.01); *G06T 7/11* (2017.01);
(Continued)

(58) Field of Classification Search
CPC ............... G06T 7/0012; G06T 7/11; G06T 2207/10056; G06T 2207/30024;
(Continued)

(56) References Cited

U.S. PATENT DOCUMENTS

| | | | |
|---|---|---|---|
| 8,693,743 B1* | 4/2014 | Younes | G16B 25/10 382/128 |
| 2011/0040544 A1 | 2/2011 | Donovan et al. | |
| 2014/0378500 A1 | 12/2014 | Cohen et al. | |
| 2017/0270666 A1 | 9/2017 | Barnes et al. | |
| 2019/0236780 A1* | 8/2019 | Barnes | G06T 7/0012 |

(Continued)

FOREIGN PATENT DOCUMENTS

WO  WO 2018/065434 A1  4/2018
WO  WO 2018/165103 A1  9/2018

OTHER PUBLICATIONS

NPL "Qaiser et al. Learning Where to See: A Novel Attention Model for Automated Immunohistochemical Scoring" (Year: 2019).*

(Continued)

*Primary Examiner* — Andrew W Bee
*Assistant Examiner* — Winta Gebreslassie
(74) *Attorney, Agent, or Firm* — Bookoff McAndrews, PLLC

(57) ABSTRACT

Systems and methods are disclosed for receiving a target electronic image corresponding to a target specimen, the target specimen comprising a tissue sample of a patient, applying a machine learning system to the target electronic image to identify a region of interest of the target specimen and determine an expression level of, category of, and/or presence of a biomarker in the region of interest, the biomarker comprising at least one from among an epithelial growth factor receptor (EGFR) biomarker and/or a DNA mismatch repair (MMR) deficiency biomarker, the machine learning system having been generated by processing a plurality of training images to predict whether a region of interest is present in the target electronic image, the training images comprising images of human tissue and/or images that are algorithmically generated, and outputting the determined expression level of, category of, and/or presence of the biomarker in the region of interest.

20 Claims, 31 Drawing Sheets

(51) Int. Cl.
*G06T 7/11* (2017.01)
*G06V 20/69* (2022.01)
*G16H 10/40* (2018.01)
*G16H 30/40* (2018.01)
*G16H 50/20* (2018.01)

(52) U.S. Cl.
CPC .......... *G06V 20/695* (2022.01); *G06V 20/698* (2022.01); *G16H 10/40* (2018.01); *G16H 30/40* (2018.01); *G16H 50/20* (2018.01); *G06T 2207/10056* (2013.01); *G06T 2207/20081* (2013.01); *G06T 2207/30024* (2013.01); *G06V 2201/03* (2022.01)

(58) Field of Classification Search
CPC .......... G06T 2207/20081; G16H 10/40; G16H 50/20; G16H 30/40; G06V 20/695; G06V 20/698; G06V 10/255; G06V 2201/03; G06K 9/6256
See application file for complete search history.

(56) References Cited

U.S. PATENT DOCUMENTS

| | | | |
|---|---|---|---|
| 2020/0258223 A1* | 8/2020 | Yip | G06T 7/11 |
| 2020/0372636 A1 | 11/2020 | Ha | |
| 2020/0388028 A1* | 12/2020 | Agus | G16H 50/20 |
| 2022/0051804 A1 | 2/2022 | Chukka et al. | |
| 2023/0230195 A1 | 7/2023 | Yip et al. | |

OTHER PUBLICATIONS

Li, Xiao-Yang et al. "Detection of epithelial growth factor receptor (EGFR) mutations on CT images of patients with lung adenocarcinoma using radiomics and/or multi-level residual convolutionary neural networks." *Journal of thoracic disease* vol. 10,12 (2018): 6624-6635. doi: 10.21037/jtd.2018.11.03.

Sharma, Harshita, et al. "Deep convolutional neural networks for automatic classification of gastric carcinoma using whole slide images in digital histopathology." Computerized Medical Imaging and Graphics 61 (2017): 2-13.

* cited by examiner

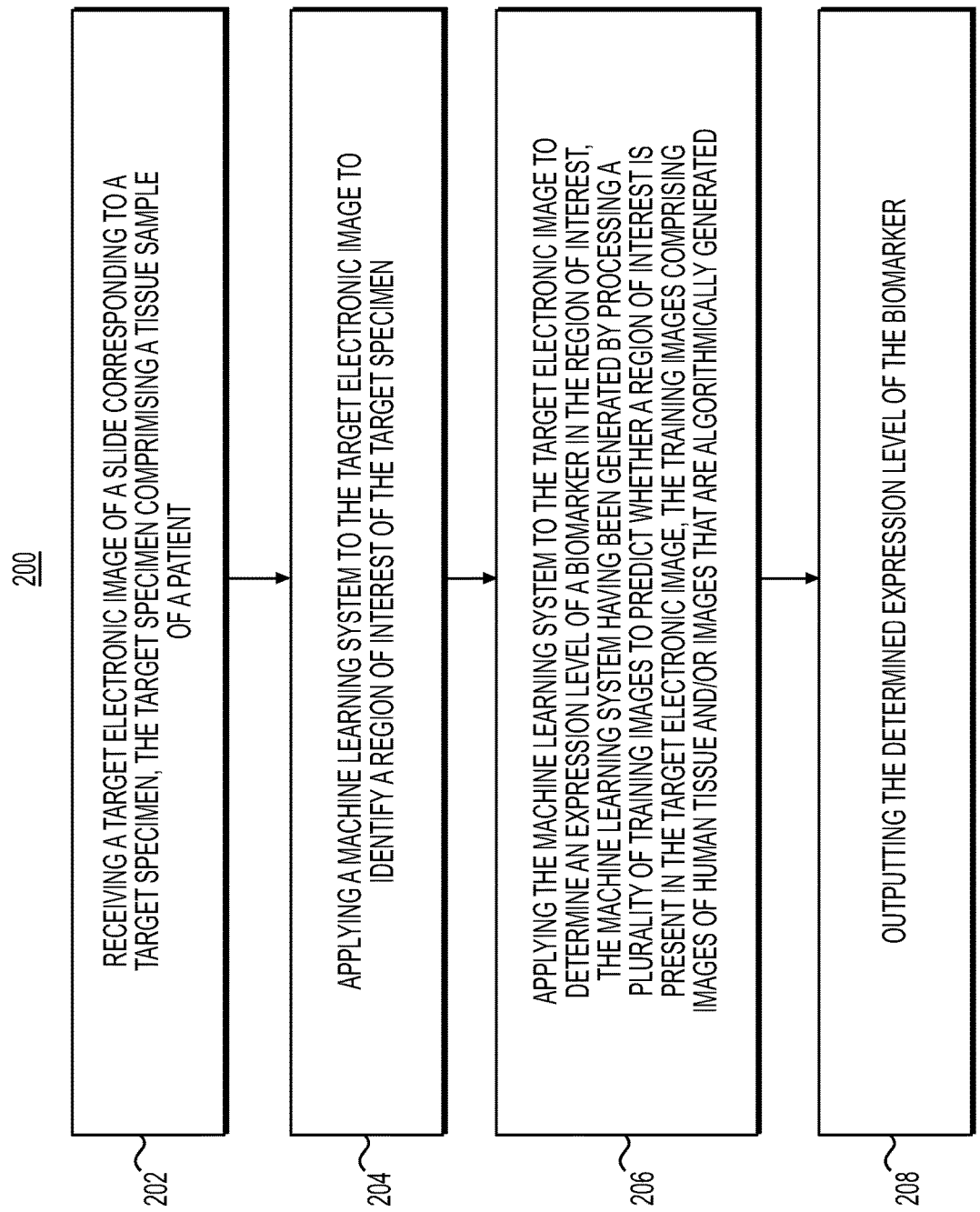

| | TRAINING (DONE AT TILE LEVEL) | | | | TEST (DONE AT TILE LEVEL) | | | | HER2 (4B5; VENTANA) |
|---|---|---|---|---|---|---|---|---|---|
| | LEVEL 0 | LEVEL 1 | LEVEL 2 | LEVEL 3 | LEVEL 0 | LEVEL 1 | LEVEL 2 | LEVEL 3 | |
| TILES* | 575,940 | 475,734 | 155,583 | 59,048 | 116,828 | 121,148 | 54,203 | 29,852 | POSITIVE (3+) |
| PARTS | 622 | 482 | 177 | 88 | 118 | 124 | 67 | 34 | EQUIVOCAL (2+). FISH WILL BE PERFORMED. |
| | | | | | | | | | EQUIVOCAL (1+ TO 2+). FISH WILL BE PERFORMED. |
| | | | | | | | | | NEGATIVE (1+) |
| | | | | | | | | | NEGATIVE (0) |

*FIG. 4F*

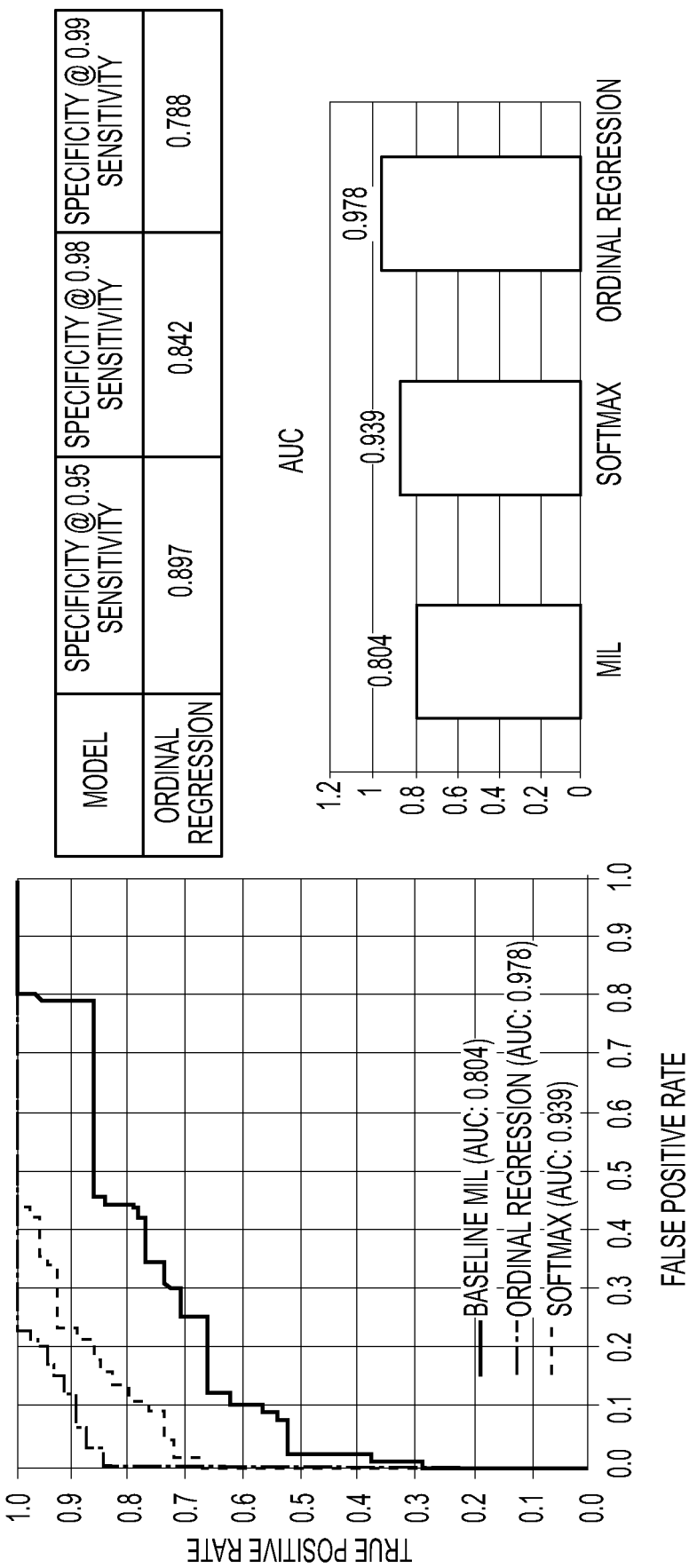

SYSTEMS AND METHODS FOR PROCESSING IMAGES OF SLIDES TO INFER BIOMARKERS

RELATED APPLICATION(S)

This application claims priority to U.S. Provisional Application No. 62/897,734 filed Sep. 9, 2019, the entire disclosure of which is hereby incorporated herein by reference in its entirety.

FIELD OF THE DISCLOSURE

Various embodiments of the present disclosure relate generally to image-based prediction of biomarkers and related image processing methods. More specifically, particular embodiments of the present disclosure relate to systems and methods for predicting one or more biomarkers based on processing images of tissue specimens.

BACKGROUND

Histological stains may be used in pathology to make cells visible. Many dye-based staining systems have been developed. However, the methods developed might not provide sufficient information for a pathologist to visually identify biomarkers that may aid diagnosis or guide treatment. Techniques such as immunohistochemistry (IHC), immunofluorescence, in situ hybridization (ISH), or fluorescence in situ hybridization (FISH), may be used. If these methods fail to provide sufficient information for detecting biomarkers, genetic testing of the tissue may be used to confirm if a biomarker is present (e.g., overexpression of a specific protein or gene product in a tumor, amplification of a given gene in a cancer, etc.). IHC is more expensive than a dye like Haemotoxylin and Eosin (H&E); however, genetic testing is even more costly and may not be available in many clinics and hospitals.

A desire exists for a method of biomarker detection that may avoid costly IHC techniques and/or genetic testing. Disclosed embodiments may use artificial intelligence (AI) to predict biomarkers (e.g., the over-expression of a protein and/or gene product, amplification, and/or mutations of specific genes) from salient regions within digital images of tissues stained using H&E and/or other dye-based methods.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for predicting one or more biomarkers from image analysis of tissue specimens.

A method for analyzing an image corresponding to a specimen includes: receiving a target electronic image corresponding to a target specimen, the target specimen comprising a tissue sample of a patient; applying a machine learning system to the target electronic image to identify a region of interest of the target specimen and determine an expression level of, category of, and/or presence of a biomarker in the region of interest, the biomarker comprising at least one from among an epithelial growth factor receptor (EGFR) biomarker and/or a DNA mismatch repair (MMR) deficiency biomarker, the machine learning system having been generated by processing a plurality of training images to predict whether a region of interest is present in the target electronic image, the training images comprising images of human tissue and/or images that are algorithmically generated; and outputting the determined expression level of, category of, and/or presence of the biomarker in the region of interest.

A system for analyzing an image corresponding to a specimen includes at least one memory storing instructions; and at least one processor executing the instructions to perform a process including receiving a target electronic image corresponding to a target specimen, the target specimen comprising a tissue sample of a patient; applying a machine learning system to the target electronic image to identify a region of interest of the target specimen and determine an expression level of, category of, and/or presence of a biomarker in the region of interest, the biomarker comprising at least one from among an epithelial growth factor receptor (EGFR) biomarker and/or a DNA mismatch repair (MMR) deficiency biomarker, the machine learning system having been generated by processing a plurality of training images to predict whether a region of interest is present in the target electronic image, the training images comprising images of human tissue and/or images that are algorithmically generated; and outputting the determined expression level of, category of, and/or presence of the biomarker in the region of interest.

A non-transitory computer-readable medium storing instructions that, when executed by processor, cause the processor to perform a method for analyzing an image corresponding to a specimen, the method includes receiving a target electronic image corresponding to a target specimen, the target specimen comprising a tissue sample of a patient; applying a machine learning system to the target electronic image to identify a region of interest of the target specimen and determine an expression level of, category of, and/or presence of a biomarker in the region of interest, the biomarker comprising at least one from among an epithelial growth factor receptor (EGFR) biomarker and/or a DNA mismatch repair (MMR) deficiency biomarker, the machine learning system having been generated by processing a plurality of training images to predict whether a region of interest is present in the target electronic image, the training images comprising images of human tissue and/or images that are algorithmically generated; and outputting the determined expression level of, category of, and/or presence of the biomarker in the region of interest.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 2A and 2B are flowcharts illustrating exemplary methods for predicting one or more biomarkers in digital pathology image(s), using machine learning, according to one or more exemplary embodiments of the present disclosure.

DESCRIPTION OF THE EMBODIMENTS

Figure 1A:
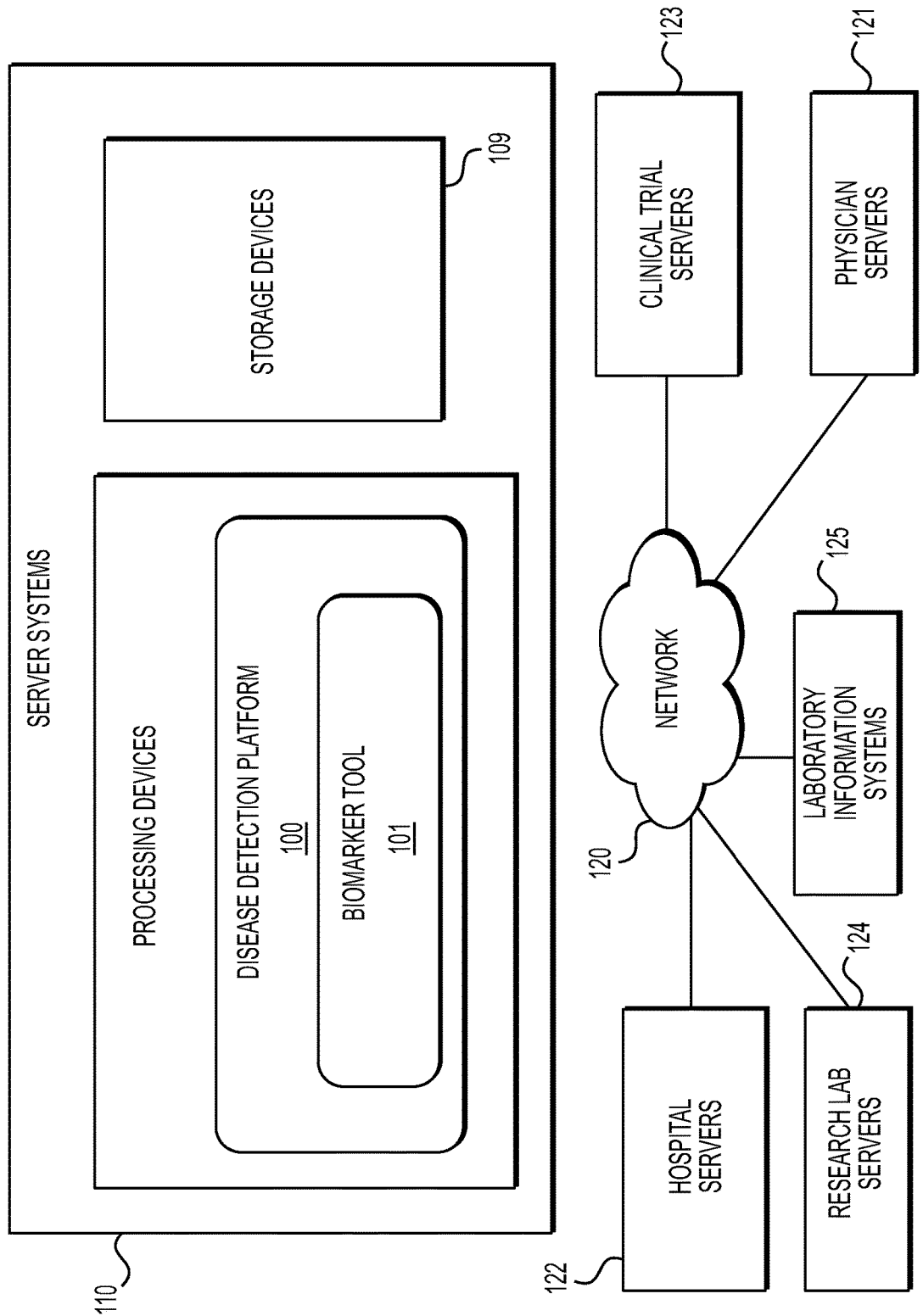
FIG. 1A illustrates an exemplary block diagram of a system and network for predicting one or more biomarkers in digital pathology image(s), according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Pathology refers to the study of diseases. More specifically, pathology refers to performing tests and analysis that are used to diagnose diseases. For example, tissue samples may be placed onto slides to be viewed under a microscope by a pathologist (e.g., a physician that is an expert at analyzing tissue samples to determine whether any abnormalities exist). That is, pathology specimens may be cut into multiple sections, stained, and prepared as slides for a pathologist to examine and render a diagnosis. When uncertain of a diagnostic finding on a slide, a pathologist may order additional cut levels, stains, or other tests to gather more information from the tissue. Technician(s) may then create new slide(s) which may contain the additional information for the pathologist to use in making a diagnosis. This process of creating additional slides may be time-consuming, not only because it may involve retrieving the block of tissue, cutting it to make a new a slide, and then staining the slide, but also because it may be batched for multiple orders. This may significantly delay the final diagnosis that the pathologist renders. In addition, even after the delay, there may still be no assurance that the new slide(s) will have information sufficient to render a diagnosis.

Pathologists may evaluate cancer and other disease pathology slides in isolation. The workflow may integrate, for example, slide evaluation, tasks, image analysis and cancer detection artificial intelligence (AI), annotations, consultations, and recommendations in one workstation.

For example, computers may be used to analyze an image of a tissue sample to quickly identify whether additional information may be needed about a particular tissue sample, and/or to highlight to a pathologist an area in which he or she should possibly look more closely. Thus, the process of obtaining additional stained slides and tests may be done automatically before being reviewed by a pathologist. When paired with automatic slide segmenting and staining machines, this may provide a fully automated slide preparation pipeline. This automation has, at least, the benefits of (1) minimizing an amount of time wasted by a pathologist determining a slide to be insufficient to make a diagnosis, (2) minimizing the (average total) time from specimen acquisition to diagnosis by avoiding the additional time between when additional tests are ordered and when they are produced, (3) reducing the amount of time per recut and the amount of material wasted by allowing recuts to be done while tissue blocks (e.g., pathology specimens) are in a cutting desk, (4) reducing the amount of tissue material wasted/discarded during slide preparation, (5) reducing the cost of slide preparation by partially or fully automating the procedure, (6) allowing automatic customized cutting and staining of slides that might result in more representative/informative slides from samples, (7) allowing higher volumes of slides to be generated per tissue block, contributing to more informed/precise diagnoses by reducing the overhead of requesting additional testing for a pathologist, and/or (8) identifying or verifying correct properties (e.g., pertaining to a specimen type) of a digital pathology image, etc.

The process of using computers to assist pathologists is known as computational pathology. Computing methods used for computational pathology may include, but are not limited to, statistical analysis, autonomous or machine learning, and AI. AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

Histopathology refers to the study of a specimen that has been placed onto a slide. For example, a digital pathology image may be comprised of a digitized image of a microscope slide containing the specimen (e.g., a smear). One method a pathologist may use to analyze an image on a slide is to identify nuclei and classify whether a nucleus is normal (e.g., benign) or abnormal (e.g., malignant). To assist pathologists in identifying and classifying nuclei, histological stains may be used to make cells visible. Dye-based staining systems have been developed, including periodic acid-Schiff reaction, Masson's trichrome, nissl and methylene blue, and Haemotoxylin and Eosin (H&E). For medical diagnosis, H&E is a widely used dye-based method, with hematoxylin staining cell nuclei blue, eosin staining cytoplasm and extracellular matrix pink, and other tissue regions taking on variations of these colors. IHC and immunofluorescence involve, for example, using antibodies that bind to specific antigens in tissues enabling the visual detection of cells expressing specific proteins of interest, which may reveal biomarkers that are not reliably identifiable to trained pathologists based on the analysis of H&E stained slides. ISH and FISH may be employed to assess the number of copies of genes or the abundance of specific RNA molecules, depending on the type of probes employed (e.g., DNA probes for gene copy number and RNA probes for the assessment of RNA expression).

A digitized image may be prepared to show a stained microscope slide, which may allow a pathologist to manually view the image on a slide and estimate a number of stained abnormal cells in the image. However, this process may be time consuming and may lead to errors in identifying abnormalities because some abnormalities are difficult to detect. Computational processes and devices may be used to assist pathologists in detecting abnormalities that may otherwise be difficult to detect.

The detected biomarkers and/or the image alone may be used to recommend specific cancer drugs and/or drug combination therapies to be used to treat a patient, and the AI may identify which drugs and/or drug combinations are unlikely to be successful by correlating the detected biomarkers with a database of treatment options. This may be used to facilitate the automatic recommendation of immunotherapy drugs to target a patient's specific cancer. Further, this may be used for enabling personalized cancer treatment for specific subsets of patients and/or rarer cancer types.

As described above, the present disclosure may use AI to predict biomarkers (e.g., the over-expression of a protein and/or gene product, amplification, or mutations of specific genes) from salient regions within digital images of tissues stained using H&E and other dye-based methods. The images of the tissues may be whole slide images (WSI), images of tissue cores within microarrays and/or selected areas of interest within a tissue section. Using staining methods like H&E, biomarkers may be difficult to visually detect or quantify without additional testing. Using AI to infer these biomarkers from digital images of tissues may improve patient care, while being faster and less expensive.

The presently disclosed AI may simultaneously infer one or more biomarkers from the same digital image of a pathology specimen comprising H&E-stained histologic sections (e.g. whole tissue sections, microarray cores and/or areas of interest within a tissue preparation). For example, given an H&E stained whole slide digital image of a breast cancer specimen, the AI of the present disclosure may infer a specimen's HER2 status, ER status, PR status, inflammatory infiltrate (and its composition), as well as a resistance or response to specific therapies, such as hormone therapy, anti-HER2 agents, CDK4/6 inhibitors, immune-checkpoint inhibitors and Chimeric antigen receptor T (CART-T) cell-based therapy, and more. This may mean that an exhaustive suite of tests using IHC and other techniques can be avoided because the biomarkers may be inferred from the H&E image alone. The detected biomarkers or the image alone may then be used to recommend specific breast cancer drugs or drug combination therapies to be used to treat a patient, and the AI may identify which drugs or drug combinations are unlikely to be successful by correlating the detected biomarkers with a database of treatment options. This may be used to facilitate the automatic recommendation of immunotherapy drugs to target a patient's specific cancer. The above-described methods may be useful for enabling personalized cancer treatment for specific subsets of patients and/or rarer cancer types.

The present exemplary embodiments may include salient region detection to identify the regions of the image for which the biomarker may be identified. For example, biomarkers of diagnostic relevance may be inferred from cancerous tissues, and other tissues may be less relevant to identification of the biomarker. Salient region detection may enable better sample complexity so that a machine learning model and/or system may be effectively trained to identify the biomarker(s) of interest from relevant tissue (e.g., cancer tissue), with less relevant tissue excluded from analysis.

According to one or more exemplary embodiments, biomarker detection may be less expensive because biomarkers may be detected using H&E alone, thus enabling biomarkers to be detected in a reproducible and deterministic manner. When scoring an IHC, immunofluorescence, ISH and FISH, there may be variability among pathologists, which may impair both treatment recommendation and/or drug research.

FIG. 1A illustrates a block diagram of a system and network for predicting one or more biomarkers in digital pathology image(s), using machine learning, according to an exemplary embodiment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present application, the electronic network 120 may also be connected to server systems 110, which may include processing devices that are configured to implement a disease detection platform 100, which includes a biomarker tool 101 for predicting one or more biomarkers in digital pathology image(s), using machine learning, according to an exemplary embodiment of the present disclosure.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for a disease detection platform 100, according to one embodiment. Alternatively, or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides.

Figure 1B:
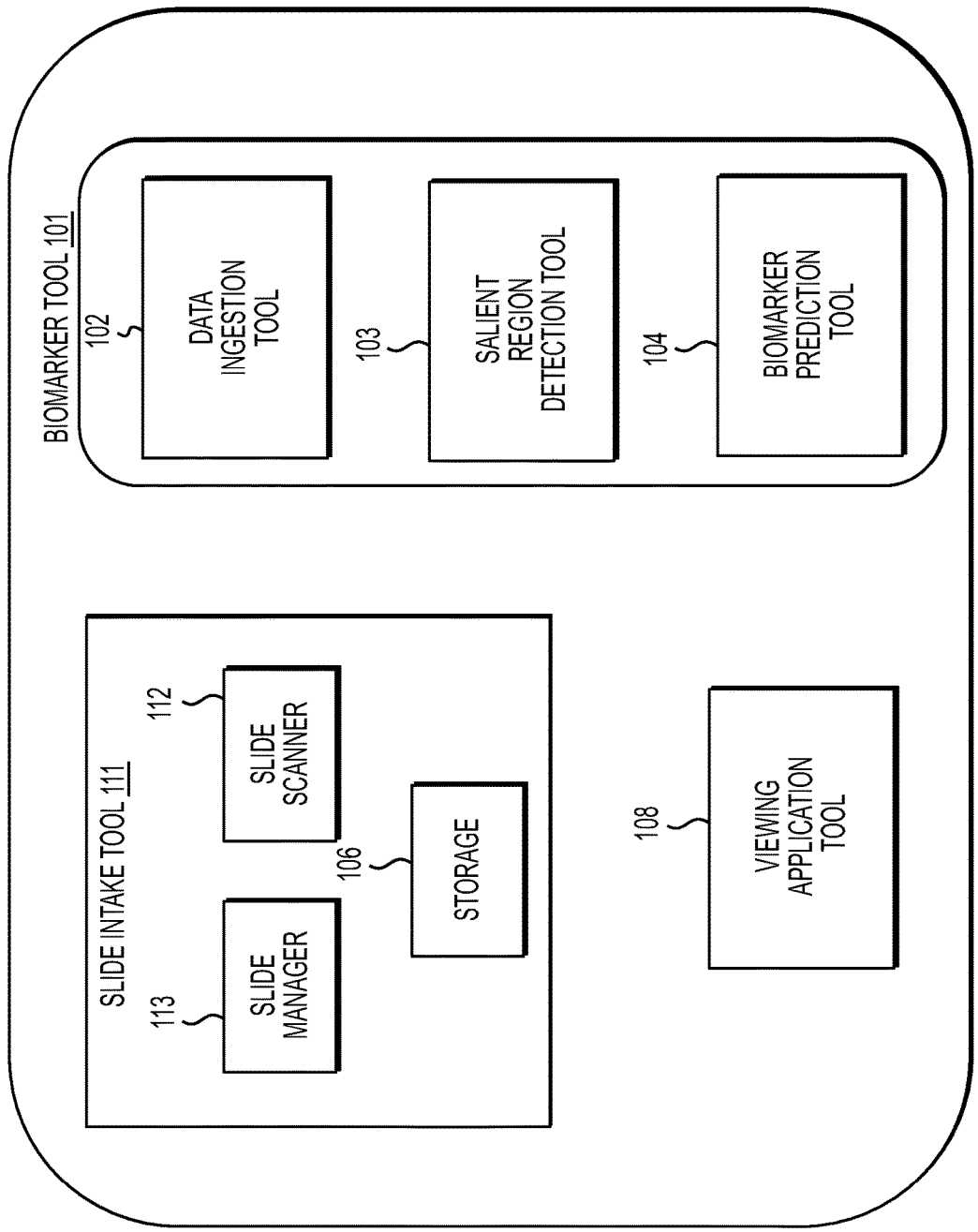
FIG. 1B illustrates an exemplary block diagram of a disease detection platform 100, according to an exemplary embodiment of the present disclosure.

FIG. 1B illustrates an exemplary block diagram of a disease detection platform 100 for predicting one or more biomarkers in digital pathology image(s), using machine learning.

Specifically, FIG. 1B depicts components of the disease detection platform 100, according to one embodiment. For example, the disease detection platform 100 may include a biomarker tool 101, a data ingestion tool 102, a salient region detection tool 103, a biomarker prediction tool 104, a storage 106, a viewing application tool 108, a slide intake tool 111, a slide scanner 112, and/or a slide manager 113.

The biomarker tool 101, as described below, refers to a process and system for predicting one or more biomarkers in digital pathology image(s), using machine learning, according to an exemplary embodiment.

The data ingestion tool 102 refers to a process and system for facilitating a transfer of the digital pathology images to the various tools, modules, components, and devices that are used for predicting one or more biomarkers in the digital pathology images, according to an exemplary embodiment.

The salient region detection tool 103 may identify salient regions of one or more digital images to be analyzed. This detection may be performed manually by a human or automatically using AI. An entire image or specific image regions may be considered salient. The image region salient to biomarker detection, e.g., region with a tumor, may take a fraction of an entire image. Regions of interest may be specified by a human expert using an image segmentation mask, a bounding box, or a polygon. Alternatively, or in addition, AI may provide a complete end-to-end solution in identifying locations. Salient region identification may enable the downstream AI system to learn how to detect biomarkers from less annotated data and to make more accurate predictions. Exemplary embodiments may include: (1) strongly supervised methods that identify precisely where the biomarker may be found; and/or (2) weakly supervised methods that may not provide a precise location. During AI training, the strongly supervised system may receive as input, the image and the location of the salient regions that may potentially express the biomarker. These locations may be specified with pixel-level labeling, bounding box-based labeling, polygon-based labeling, and/or using a corresponding image where the saliency has been identified (e.g., using IHC). The weakly supervised system may receive as input, the image or images and the presence/absence of the salient regions. The exact location of the salient location in one or more images may be unspecified when training the weakly supervised system.

The biomarker prediction tool 104 may predict and/or infer biomarker presence using machine learning and/or computer vision. The prediction may be output to an electronic storage device. A notification or visual indicator may be sent/displayed to a user, alerting the user to the presence or absence of one or more of the biomarkers.

The slide intake tool 111 refers to a process and system for scanning pathology images and converting them into a digital form, according to an exemplary embodiment. The slides may be scanned with slide scanner 112, and the slide manager 113 may process the images on the slides into digitized pathology images and store the digitized images in storage 106.

The viewing application tool 108 refers to a process and system for providing a user (e.g., pathologist) with specimen property or image property information pertaining to digital pathology image(s), according to an exemplary embodiment. The information may be provided through various output interfaces (e.g., a screen, a monitor, a storage device, and/or a web browser, etc.).

The biomarker tool 101, and each of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the biomarker tool 101, the data ingestion tool 102, the slide intake tool 111, the slide scanner 112, the slide manager 113, and viewing application tool 108. Server systems 110 may also include processing devices for processing images and data stored in the storage devices. Server systems 110 may further include one or more machine learning tool(s) or capabilities, e.g., due to the processing devices. Alternatively, or in addition, the present disclosure (or portions of the system and methods of the present disclosure) may be performed on a local processing device (e.g., a laptop).

Any of the above devices, tools, and modules may be located on a device that may be connected to an electronic network 120, such as the Internet or a cloud service provider, through one or more computers, servers, and/or handheld mobile devices.

Figure 1C:
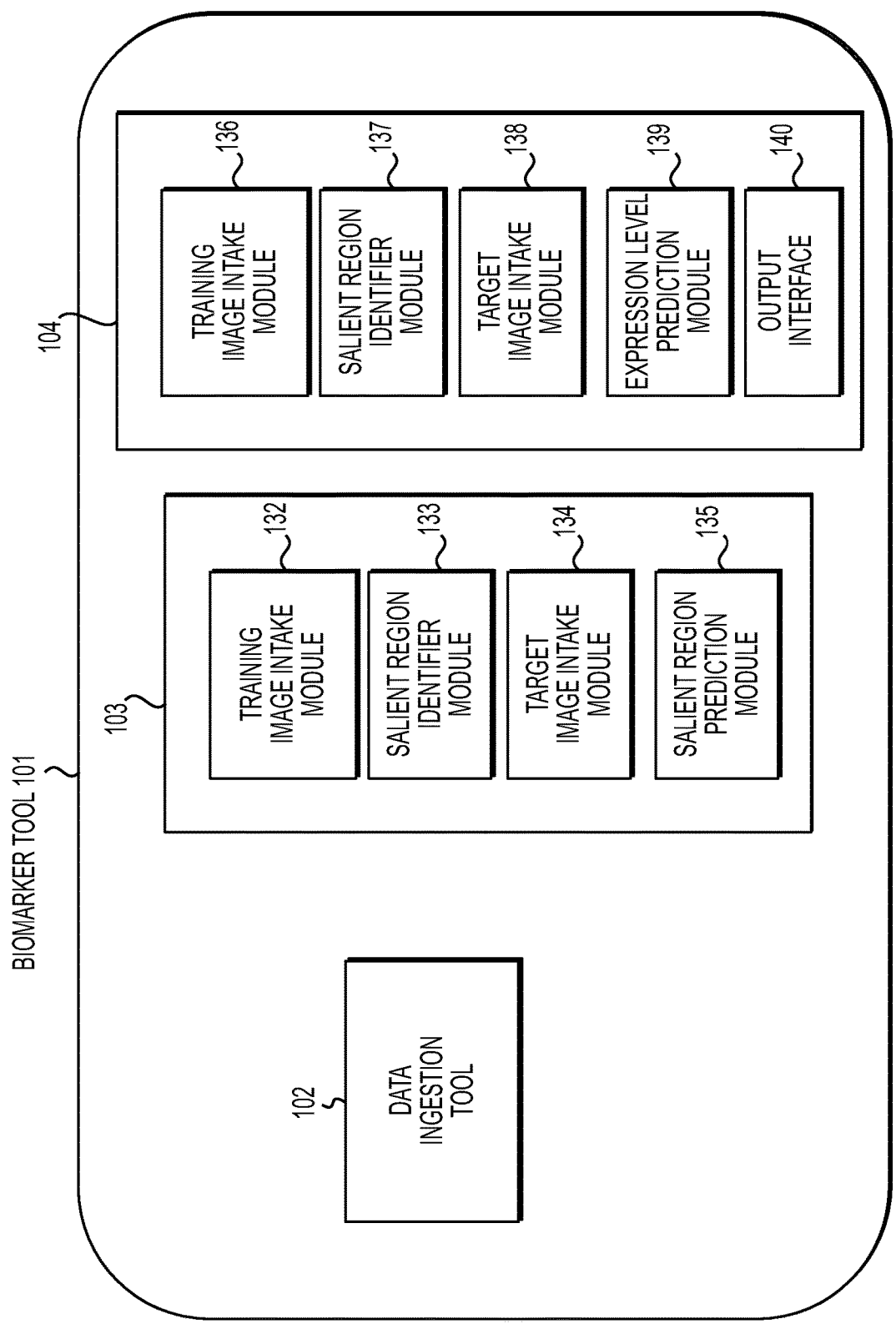
FIG. 1C illustrates an exemplary block diagram of a biomarker tool 101, according to an exemplary embodiment of the present disclosure.

FIG. 1C illustrates an exemplary block diagram of a biomarker tool 101, according to an exemplary embodiment of the present disclosure. The biomarker tool 101 may include the data ingestion tool 102, the salient region detection tool 103, and/or the biomarker prediction tool 104.

The salient region detection tool 103 may include a training image intake module 132, a salient region identifier module 133, a target image intake module 134, and/or a salient region prediction module 135.

The training image intake module 132 may receive one or more digital images of a pathology specimen (e.g., histology, cytology, etc.) into a digital storage device (e.g., hard drive, network drive, cloud storage, RAM, etc.), and may receive, for one or more images, an indication of the presence or absence of the salient region (e.g., disease present somewhere in the image). For example, the training image intake module 132 may break one or more digital images into sub-regions. One or more sub-regions may have saliency determined. Regions may be specified in a variety of methods, including creating tiles of the image, segmentations based edge/contrast, segmentations via color differences, supervised determination by the machine learning system, and/or EdgeBoxes, etc.

The salient region identifier module 133 may train a machine learning algorithm that takes, as input, a digital image of a pathology specimen and predicts whether the salient region is present or not. Many methods may be used to learn which regions are salient, including but not limited to: (1) weak supervision: training a machine learning system (e.g., multi-layer perceptron (MLP), convolutional neural network (CNN), graph neural network, support vector machine (SVM), random forest, etc.) using multiple instance learning (MIL) using weak labeling of the digital image or a collection of images; the label may correspond to the presence or absence of a salient region that may express the relevant biomarker; (2) bounding box or polygon-based supervision: training a machine learning system (e.g., region-based CNN (R-CNN), Faster R-CNN, Selective Search) using bounding boxes or polygons that specify the sub-regions of the digital image that are salient for the detection of the presence or absence of the biomarker; (3) pixel-level labeling (e.g., a semantic or instance segmentation): training a machine learning system (e.g., Mask R-CNN, U-Net, Fully Convolutional Neural Network) using a pixel-level labeling, where individual pixels are identified as being salient for the detection of the biomarker; and/or (4) using a corresponding, but different digital image that identifies salient tissue regions—a digital image of tissue that highlights the salient region (e.g., cancer identified using IHC) may be registered with the input digital image. For example, a digital image of an H&E image may be registered/aligned with an IHC image identifying salient tissue (e.g., cancerous tissue where the biomarker should be found), where the IHC may be used to determine the salient pixels based on image color characteristics.

The target image intake module 134 may receive one or more digital images of a pathology specimen (e.g., histology, cytology, etc.) into a digital storage device (e.g., hard drive, network drive, cloud storage, RAM, etc.). One or more digital images may be divided into sub-regions, and a saliency of one or more sub-regions may be determined (e.g., cancerous tissue for which the biomarker(s) should be identified). Regions may be specified in a variety of methods, including creating tiles of the image, segmentations based edge/contrast, segmentations via color differences, supervised determination by the machine learning system, and/or EdgeBoxes, etc.

The salient region prediction module 135 may apply a trained machine learning algorithm to the image/sub-region to predict which regions of the image are salient and may potentially exhibit the biomarker(s) of interest (e.g., cancerous tissue). If a salient regions is present, identify and flag the location of the salient region. The salient regions may be detected using a variety of methods, including but not limited to: (1) running the machine learning system on image sub-regions to generate the prediction for one or more sub-regions; and/or (2) using machine learning visualization tools to create a detailed heatmap, e.g., by using class activation maps, GradCAM, etc., and then extracting the relevant regions.

The biomarker prediction tool 104 may include a training image intake module 136, a salient region identifier module 137, a target image intake module 138, an expression level prediction module 139, and/or an output interface 140.

The training image intake module 136 may receive one or more digital images of a pathology specimen (e.g., histology, cytology, etc.) into a digital storage device (e.g., hard drive, network drive, cloud storage, RAM, etc.), and may receive, for one or more images, the level of a biomarker present (e.g., binary or ordinal value). For example, one or more digital images may be broken into sub-regions. One or more sub-regions may have their saliency determined. Regions may be specified in a variety of methods, including creating tiles of the image, segmentations based edge/contrast, segmentations via color differences, supervised determination by the machine learning system, and/or EdgeBoxes, etc.

The salient region identifier module 137 may identify salient regions that may be relevant to biomarker(s) of interest using an AI-based system and/or using manual annotations from an expert. A machine learning algorithm may be trained to predict the expression level of one or more biomarkers from the (salient) image regions. Expression levels may be represented as binary numbers, ordinal numbers, real numbers, etc. Techniques presented herein may be implemented in multiple ways, including but not limited to: CNN, CNN trained with MIL, recurrent neural network (RNN), long-short term memory RNN (LSTM), gated recurrent unit RNN (GRU), graph convolutional network, support vector machine, and/or random forest.

The target image intake module 138 may receive one or more digital images of a pathology specimen (e.g., histology, cytology, etc.) into a digital storage device (e.g., hard drive, network drive, cloud storage, RAM, etc.), and receive the location of salient region, which may be automatically identified using AI and/or manually specified by an expert.

The expression level prediction module 139 may apply a machine learning algorithm to provide a prediction of whether the biomarker is present.

The output interface 140 may output a prediction of whether a biomarker is present to an electronic storage device. For example, the output interface 140 may display a visual indicator to alert a user (e.g., a pathologist, histology technician, etc.) to a presence of the biomarker.

FIG. 2A is a flowchart illustrating an exemplary method of a tool for predicting one or more biomarkers, according to an exemplary embodiment of the present disclosure. For example, an exemplary method 200 (e.g., steps 202 to 208) may be performed by the biomarker tool 101 automatically or in response to a request from a user (e.g., physician, pathologist, technician, etc.).

According to one embodiment, the exemplary method 200 for predicting a biomarker may include one or more of the following steps. In step 202, the method may include receiving a target electronic image of a slide corresponding to a target specimen, the target specimen comprising a tissue sample of a patient. For example, the target electronic image may be received from any one or any combination of the server systems 110, physician servers 121, hospital servers 122, clinical trial servers 123, research lab servers 124, and/or laboratory information systems 125.

In step 204, the method may include applying a machine learning system to the target electronic image to identify a region of interest (e.g., salient region) of the target specimen. In step 206, the method may include applying the machine learning system to the target electronic image to determine an expression level of a biomarker in the region of interest. In step 208, the method may include outputting the determined expression level of the biomarker.

The machine learning system may have been generated by processing a plurality of training images to predict whether a region of interest is present in the target electronic image, and the training images may include images of human tissue and/or images that are algorithmically generated. The machine learning system may be implemented using machine learning methods for classification and regression. Training inputs may include real or synthetic imagery. Training inputs may or may not be augmented (e.g., adding noise or creating variants of the input by flipping/distortions). Exemplary machine learning systems may include, but are not limited to, any one or any combination of Neural Networks, Convolutional neural networks, Random Forest, Logistic Regression, and Nearest Neighbor. Convolutional neural networks may directly learn the image feature representations necessary for discriminating among characteristics, which may work extremely well when there are large amounts of data to train on for each specimen, whereas the other methods may be used with traditional computer vision features, e.g., scale invariant feature transform (SURF) and/or speed up robust feature (SIFT), and/or with learned embeddings (e.g., descriptors) produced by a trained convolutional neural network, which may yield advantages when there are only small amounts of data to train on. The training images may be received from any one or any combination of the server systems 110, physician servers 121, hospital servers 122, clinical trial servers 123, research lab servers 124, and/or laboratory information systems 125. This dataset may be kept on a digital storage device. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, IHC, molecular pathology, etc.; and/or (b) digitized tissue samples from a 3D imaging device, such as microCT.

Figure 2B:
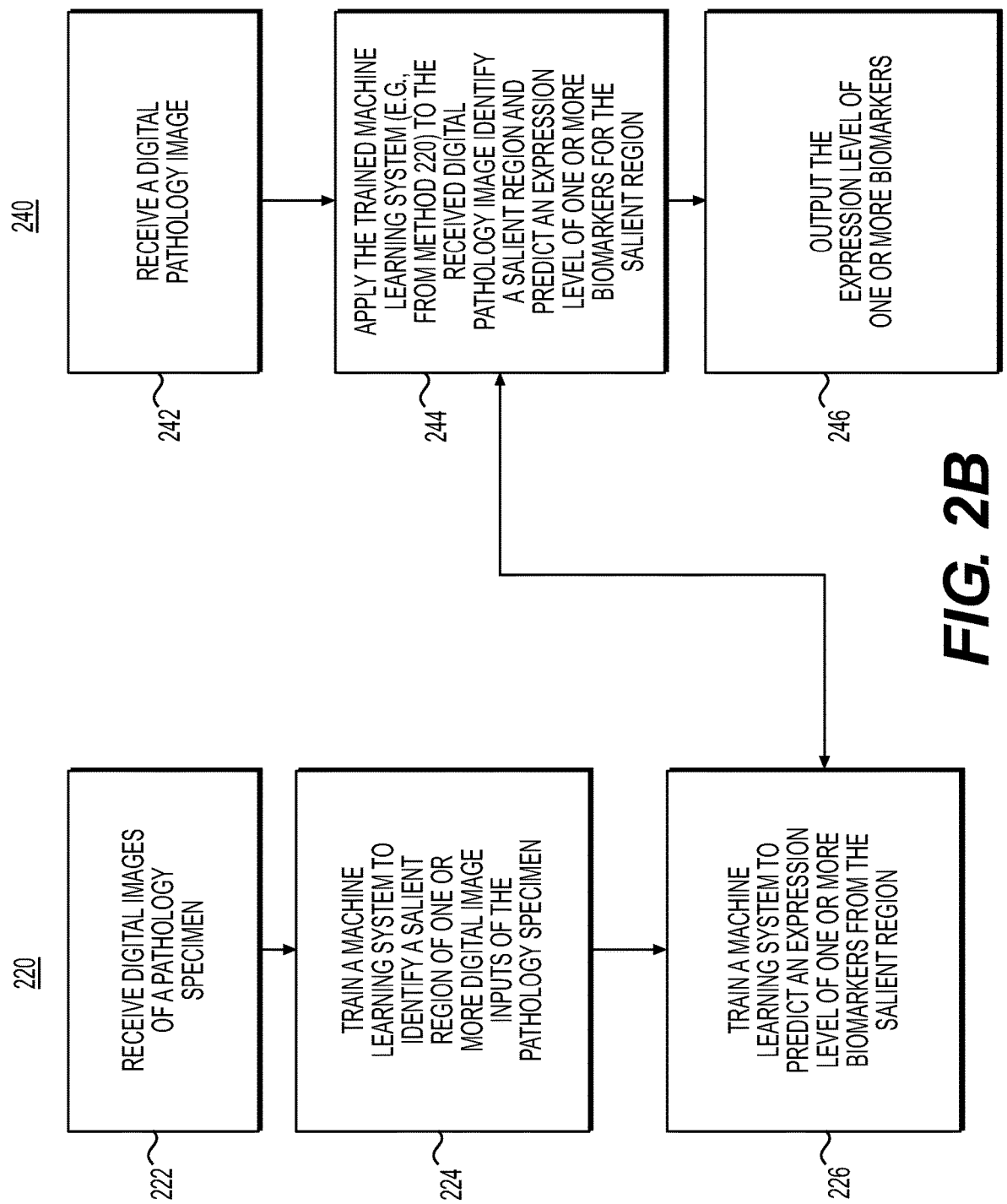

As illustrated in FIG. 2B, according to one embodiment, exemplary methods 220 and 240 for predicting a biomarker may include one or more of the steps below. In step 222, during a training phase, the method may include a data ingestion process, which may include receiving one or more digital images of a pathology specimen (e.g., histology, cytology, etc.) into a digital storage device (e.g., hard drive, network drive, cloud storage, RAM, etc.). For training the machine learning system, one or more images may be paired with information about its biomarkers (e.g., from genetic testing, from IHC results analyzed by a pathologist, clinician annotations, etc.). One or more digital images may be broken into sub-regions and one or more sub-regions may have their saliency determined. Regions may be specified in a variety of methods, including creating tiles of the image, segmentations based edge/contrast, segmentations via color differences, supervised determination by the machine learning system, and/or EdgeBoxes, etc.

In step 224, during a training phase, the method may include training a machine learning system to detect and/or identify a salient region of one or more digital image inputs of the pathology specimen, using an AI-based method and/or manual specification. An entire image or specific image regions may be considered salient. The image region salient to biomarker detection, e.g., a tumor, may take a fraction of the entire image. Regions of interest may be specified by a human expert using an image segmentation mask, a bounding box, or a polygon. Alternatively, AI may provide a complete end-to-end solution in identifying locations. Salient region identification may enable the downstream AI system to learn how to detect biomarkers from less annotated data and to make more accurate predictions.

In step 226, the method may include training a machine learning system to predict an expression level of one or more biomarkers from the salient region(s). Expression levels may be represented as binary numbers, ordinal numbers, and/or real numbers, etc. The training method may be implemented in multiple ways. For example, according to one embodiment, the algorithm may be implemented by any one or any combination of (1) machine learning algorithms and/or architectures, such as neural network methods, e.g., convolutional neural networks (CNNs) and recurrent neural networks (RNNs); (2) training methodologies, such as Multiple Instance Learning, Reinforcement Learning, Active Learning, etc.; (3) long-short term memory RNN (LSTM); (4) gated recurrent unit RNN (GRU); (5) Graph convolutional network; (6) support vector machine; and/or (7) random forest.

According to one or more embodiments, any of the above algorithms, architectures, methodologies, attributes, and/or features may be combined with any or all of the other algorithms, architectures, methodologies, attributes, and/or features. For example, any of the machine learning algorithms and/or architectures (e.g., neural network methods, convolutional neural networks (CNNs), recurrent neural networks (RNNs), etc.) may be trained with any of the training methodologies (e.g., Multiple Instance Learning, Reinforcement Learning, Active Learning, etc.)

The description of the terms below is merely exemplary and is not intended to limit the terms in any way.

A label may refer to information about an input to a machine learning algorithm that the algorithm is attempting to predict.

For a given image of size N×M, a segmentation may be another image of size N×M that, for each pixel in an original image, assigns a number that describes the class or type of that pixel. For example, in a WSI, elements in the mask may categorize each pixel in the input image as belonging to the classes of, e.g., background, tissue and/or unknown.

Slide level information may refer to information about a slide in general, but not necessarily a specific location of that information in the slide.

A heuristic may refer to a logic rule or function that deterministically produces an output, given inputs. For example: if a prediction that a slide contains a biomarker, then output one, if not, output 0.

Embedding may refer to a conceptual high-dimensional numerical representation of low-dimensional data. For example, if a WSI is passed through a CNN training to classify tissue type and/or predict biomarkers, the numbers on the last layer of the network may provide an array of numbers (e.g., in the order of thousands) that contain information about the slide (e.g., information about a type of tissue).

Slide level prediction may refer to a concrete prediction about a slide as a whole. For example, a slide level prediction may be that the slide contains one or more biomarkers.

A classifier may refer to a model that is trained to take input data and associate it with a category.

According to one or more embodiments, the machine learning system may be trained in different ways. For example, the training of the machine learning system may be performed by any one or any combination of supervised training, semi-supervised training, unsupervised training classifier training, mixed training, and/or uncertainty estimation. The type of training used may depend on an amount of data, a type of data, and/or a quality of data. Table 1 below describes a non-limiting list of some types of training and the corresponding features.

TABLE 1

| Index | Input | Label | Model | Output |
|---|---|---|---|---|
| 1 | WSI Embedding | Segmentation | CNN, RNN, MLP | Predicted Segmentation Embedding |
| 2 | WSI Embedding | Slide Level Information | CNN, RNN, MLP | Embedding Slide level prediction |
| 3 | WSI Embedding | — | CNN, RNN, MLP | Embedding |
| 4 | Embedding | Slide Level Information | SVM, MLP, RNN, Random Forests | Slide level prediction |
| 5 | Slide level prediction | Measure of how wrong the prediction was | MLP, RNN, Statistical Model | Predict a likelihood that an original prediction is wrong |

Supervised training may be used with a small amount of data to provide a seed for a machine learning system. In supervised training, the machine learning system may look for a specific item (e.g., biomarker), and quantify how much of the specific item is present in the slide.

According to one embodiment, an example fully supervised training may take as an input a WSI and may include a label of segmentation. Pipelines for a fully supervised training may include (1) 1; (2) 1, Heuristic; (3) 1, 4, Heuristic; (4) 1, 4, 5, Heuristic; and/or (5) 1, 5, Heuristic. Advantages of a fully supervised training may be that (1) it may require fewer slides and/or (2) the output is explainable because it may be known which areas of the image contributed to the diagnosis. A disadvantage of using a fully supervised training may be that it may require large amounts of segmentation which may be difficult to acquire.

According to one embodiment, an example semi-supervised (e.g., weakly supervised) training may take as an input WSI and may include a label of slide level information. Pipelines for a semi-supervised training may include (1) 2; (2) 2, Heuristic; (3) 2, 4, Heuristic; (4) 2, 4, 5, Heuristic; and/or (5) 2, 5, Heuristic. Advantages of using a semi-supervised training may be that (1) the types of labels possibly required may be present in many hospital records; and (2) output is explainable because it may be known which areas of the image contributed most to the diagnosis. A disadvantage of using a semi-supervised training is that it may be difficult to train. For example, the model may need to use a training scheme such as Multiple Instance Learning, Activate Learning, and/or distributed training to account for the fact that there is limited information about where in the slide the information is that should lead to a decision.

According to one embodiment, an example unsupervised training may take as an input a WSI and may require no label. The pipelines for an unsupervised training may include (1) 3, 4; and/or (2) 3, 4, Heuristic. An advantage of unsupervised training may be that it does not require any labels. Disadvantages of using an unsupervised training may be that (1) it may be difficult to train. For example, it may need to use a training scheme such as Multiple Instance Learning, Activate Learning, and/or distributed training to account for the fact that there is limited information about where in the slide the information is that should lead to a decision; (2) it may require additional slides; and/or (3) it may be less explainable because it might output a prediction and probability without explaining why that prediction was made.

According to one embodiment, an example mixed training may include training any of the example pipelines described above for fully supervised training, semi-supervised training, and/or unsupervised training, and then use the resulting model as an initial point for any of the training methods. Advantages of mixed training may be that (1) it may require less data; (2) it may have improved performance; and/or (3) it may allow a mixture of different levels of labels (e.g., segmentation, slide level information, no information). Disadvantages of mixed training may be that (1) it may be more complicated and/or expensive to train; and/or (2) it may require more code that may increase a number and/or complexity of potential bugs.

According to one embodiment, an example uncertainty estimation may include training any of the example pipelines described above for fully supervised training, semi-supervised training, and/or unsupervised training, for any task related to slide data using uncertainty estimation in the end of the pipeline. Further, a heuristic or classifier may be used to predict expression levels of biomarkers based on an amount of uncertainty in the prediction of the test. An advantage of uncertainty estimation may be that it is robust to out-of-distribution data. For example, when unfamiliar data is presented, it may still correctly predict that it is uncertain. Disadvantages of uncertainty estimation may be that (1) it may need more data; (2) it may have poor overall performance; and/or (3) it may be less explainable because the model might not necessarily identify how a slide or slide embedding is abnormal.

According to one embodiment, an ensembles training may include simultaneously running models produced by any of the example pipelines described above, and combining the outputs by a heuristic or a classifier to produce robust and accurate results. Advantages of ensembles training may be that (1) it is robust to out-of-distribution data; and/or (2) it may combine advantages and disadvantages of other models, resulting in a minimization of disadvantages (e.g., a supervised training model combined with an uncertainty estimation model, and a heuristic that uses a supervised model when incoming data is in distribution and uses an uncertainty model when data is out of distribution, etc.).

Disadvantages of ensembles training may be that (1) it may be more complex; and/or (2) it may be expensive to train and run.

Training techniques discussed herein may also proceed in stages, where images with greater annotations are initially used for training, which may allow for more effective later training using slides that have fewer annotations, are less supervised, etc.

Training may begin using the slides that are the most thoroughly annotated, relative to all the training slide images that may be used. For example, training may begin using supervised learning. A first set of slide images may be received or determined with associated annotations. Each slide may have marked and/or masked regions and may include information such as identifying salient regions and predicting expression levels of biomarkers. The first set of slides may be provided to a training algorithm, for example a CNN, which may determine correlations between the first set of slides and their associated annotations.

After training with the first set of images is completed, a second set of slide images may be received or determined having fewer annotations than the first set, for example with partial annotations. In one embodiment, the annotations might only indicate that the slide has a salient region, but might not specify what or where disease may be found, etc. The second set of slide images may be trained using a different training algorithm than the first, for example Multiple Instance Learning. The first set of training data may be used to partially train the system, and may make the second training round more effective at producing an accurate algorithm.

In this way, training may proceed in any number of stages, using any number of algorithms, based on the quality and types of the training slide images. These techniques may be utilized in a situations where multiple training sets of images are received, which may be of varying quality, annotation levels, and/or annotation types.

According to one embodiment illustrated in 2B, an exemplary method 240 for using the tool may include one or more of the steps below. According to one embodiment, an exemplary method 240 for using the biomarker tool to predict one or more biomarkers may include one or more of the steps below. In step 242, the method may include receiving one or more digital images of a pathology specimen (e.g., histology, cytology, etc.) in a digital storage device (e.g., hard drive, network drive, cloud storage, RAM, etc.), and receiving a location of salient region, using an AI-based method and/or manual specification. In step 244, the method may include applying the salient region detector machine learning algorithm (e.g., method 220) to the image to predict if cancer is possibly present in the received images and to identify salient image regions that may correspond to cancerous tissue using an AI-based method and/or manual specification. Additionally, the method may include applying the machine learning biomarker detection algorithm (e.g., method 220) to the image to determine a prediction of a biomarker's expression level.

In step 246, the method may include outputting the prediction to an electronic storage device. The method may include displaying a visual indicator to alert the user (e.g., a pathologist, histology technician, etc.) of the presence of one or more biomarkers and/or expression levels of one or more biomarkers.

Figure 3A:
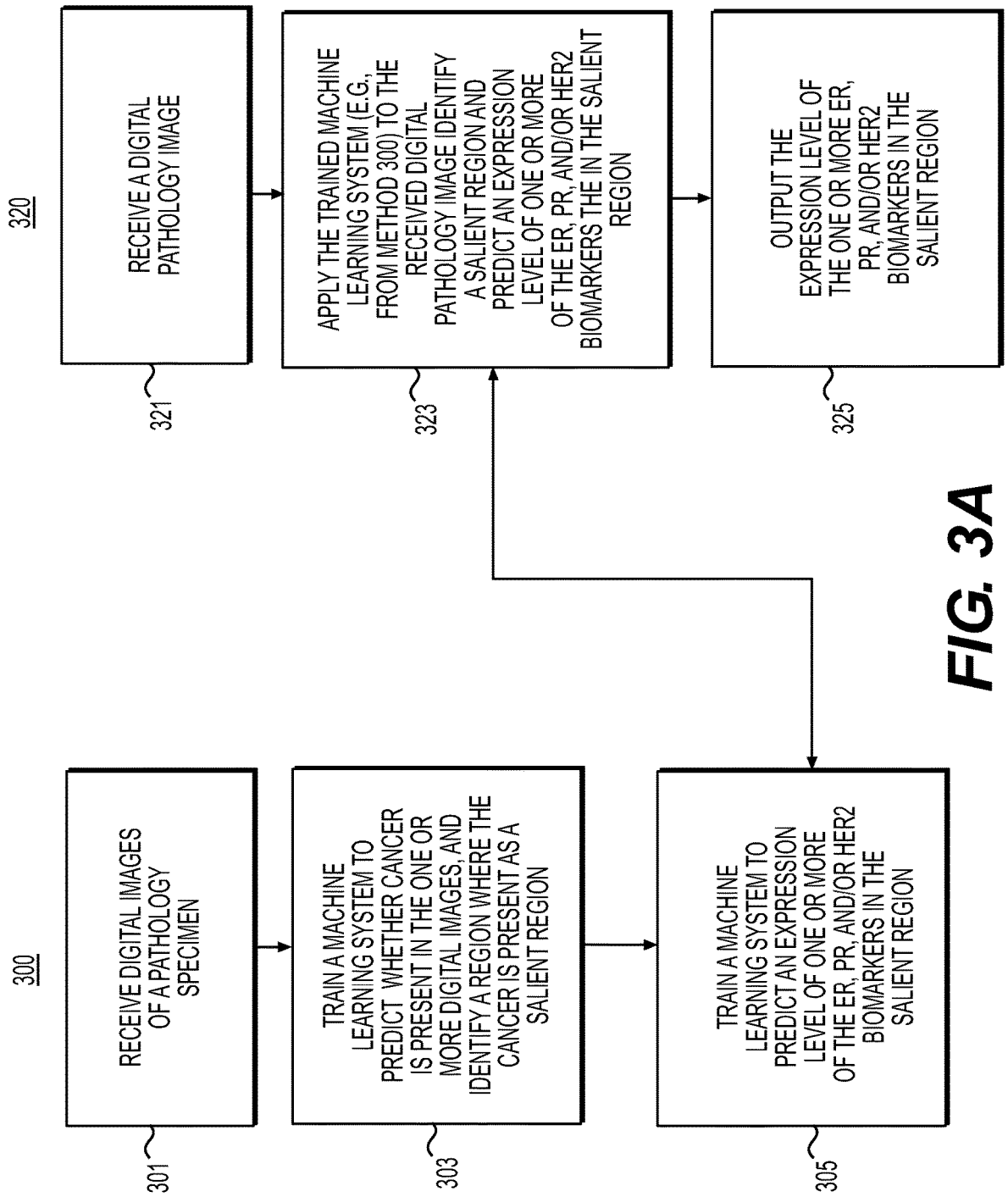
FIG. 3A is a flowchart illustrating an exemplary method for predicting estrogen receptor (ER), progesterone receptor (PR), and/or human epidermal growth factor receptor 2 (HER2, which may be known as ERBB2) biomarkers, according to an exemplary embodiment of the present disclosure.

As illustrated in FIG. 3A, according to one embodiment, exemplary methods 300 and 320 for predicting estrogen receptor (ER), progesterone receptor (PR), and/or human epidermal growth factor receptor 2 (HER2, which may be known as ERBB2) are described below.

IHC may be used by pathologists to identify an expression of biomarkers in tumor tissue. For breast cancer, biomarkers may include ER, PR, and/or HER2. In addition, patients with ER-positive/HER2-negative disease may require further assessment of the tumor on the basis of gene signatures (e.g. Oncotype DX, Mammaprint, Endopredict, Breast Cancer Index and/or ProSigna ROR). If one of these tests predicts a low risk of metastasis, then hormone therapy alone may be considered; otherwise, a more aggressive treatment plan involving both chemotherapy and/or hormone therapy may be recommended.

Although H&E may be part of a pathologist's typical workflow, it may be difficult for pathologists to visually identify a presence of the biomarkers from H&E stains. Even IHC may be ambiguous, and additional genetic testing of the tissue may be needed. For example, when IHC is used for HER2, a reading by the pathologist might not be definitive, resulting in a subsequent test using FISH to determine if the cells have extra copies of the HER2 gene. Although IHC is expensive, FISH is more expensive; however, FISH enables a presence of HER2 gene amplification and overexpression to be determined definitively. Determining an expression of ER, PR, and/or HER2 protein overexpression and/or gene amplification may be useful for prescribing medical treatment to breast cancer patients. Techniques presented herein may be used to predict over-expression of ER, PR, and/or HER2, and the results of the gene signatures from H&E stained digital images. This may allow the identification of patients who might be eligible to receive endocrine, CDK4/6-inhibitor therapy, anti-HER2 therapy and/or chemotherapy, as well as defining patients with "triple-negative" disease, without a need for three separate IHC tests (one for ER, one for PR, and one for HER2) and/or gene signatures.

Techniques present herein may be used to detect premalignant and malignant breast tissue, and breast cancer metastatic to other sites. Further, techniques presented herein may be used to detect overexpression of these biomarkers in other tissues (e.g., HER2 amplification is also regularly assayed in gastric cancer tissue, and HER2 is known to be amplified and overexpressed in some forms of ovarian, lung, and/or uterine cancers). Techniques presented herein may be used to enable deterministic quantification of these biomarkers.

Exemplary methods may utilize the salient region detection tool 103 to identify tissue regions where cancer may be suspected. This may greatly reduce the sample complexity for the machine learning task, enabling biomarkers to be more efficiently learned by the biomarker prediction tool 104, e.g., a CNN. Techniques presented herein may be used to predict the results of gene signatures or identify the patients for testing with approved gene signatures (e.g. Oncotype DX Breast Recurrence Score test and/or the MammaPrint test). Techniques presented herein may enable the determination of eligibility for the MammaPrint test or eligibility for the Oncotype DX Breast Recurrence Score test to be assessed, in part, directly from an H&E image of a breast tumor, without the need for IHC or FISH.

Exemplary methods 300 and 320 may include one or more of the steps below. In step 301, during a training phase, the method may include receiving one or more digital images of a tissue specimen stained with H&E into a digital storage device (e.g., hard drive, network drive, cloud storage, RAM, etc.), and receiving, for one or more images, an indication of the presence or absence of the salient region, e.g., cancerous tissue. One or more digital images may be broken into sub-regions and the saliency of one or more sub-regions may be determined. The images may include cancer recurrence scores produced from genomic assays. Regions may be specified in a variety of methods, including creating tiles of the image, segmentations based edge/contrast, segmentations via color differences, supervised determination by the machine learning system, and/or Edge-Boxes, etc.

In step 303, the method may include training a machine learning algorithm that takes, as input, a digital image of a pathology specimen stained with H&E and predicting whether a salient region exists, e.g., whether cancer is possibly present, using an AI-based method and/or manual specification. The machine learning algorithm may be performed in a weakly-supervised or strongly-supervised manner.

In step 305, the method may include training the machine learning algorithm to predict an expression level of one or more of the ER, PR, and/or HER2 biomarkers based on the salient regions of the digital image of the pathology specimen and the received biomarker/score information. The method may include receiving an indication for each slide of the expression of one or more of the biomarkers, e.g., ER, PR, and/or HER2. The level of biomarker expression may be identified using IHC, FISH, or some additional orthogonal technique. The level of expression may be on a numeric, ordinal, or binary scale. The indication may be assigned to the entire image and/or image subregions, e.g., the image may be split into tiles and each tile may be assigned the HER2 overexpression level. The indication may include categorical data, e.g., "low risk" or "high risk." For example, an indication may include results of Oncotype DX. Such results may include a continuous score with predetermined or user-determined thresholds for low, intermediary and/or high risk.

According to one embodiment, an exemplary method 320 for using the biomarker tool to predict ER, PR, and/or HER2 biomarkers may include one or more of the steps below. In step 321, the method may include receiving one or more digital images of an H&E stained pathology specimen (e.g., breast cancer pathology specimen) into a digital storage device (e.g., hard drive, network drive, cloud storage, RAM, etc.). In step 323, the method may include applying the salient region detector machine learning algorithm (e.g., method 300) to the image to predict if cancer is possibly present in the received images and to identify salient image regions that may correspond to cancerous tissue using an AI-based method and/or manual specification. Additionally, the method may include applying the machine learning biomarker detection algorithm (e.g., method 300) to the image to determine a prediction of a biomarker's expression level. The method may include grouping expression levels into diagnostic categories. For example, HER2 may be graded using IHC on a scale of 0, 1+, 1+ to 2+, 2+, and/or 3+. Using a probabilistic ordinal regression model, the probability of various combinations may be computed, e.g., a probability that the score is greater than zero may be computed. This may be useful because an effectiveness of some drugs are dependent on the level of expression.

In step 325, the method may include outputting the prediction to an electronic storage device. The method may include displaying a visual indicator to alert the user (e.g., a pathologist, histology technician, etc.) of the expression levels of one or more biomarkers and/or recommending treatments that are potentially effective for the cancer given the biomarkers present.

Figure 3B:
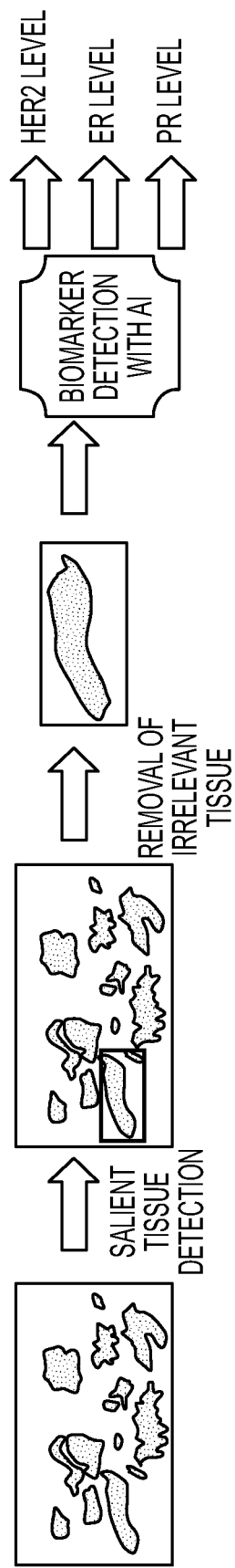
FIG. 3B. illustrates an exemplary system and method for training to identify HER2, ER, and PR overexpression levels, according to an exemplary embodiment of the present disclosure.

FIG. 3B illustrates a system and method for training to identify HER2, ER, and/or PR overexpression levels. For example, as shown at the left side of FIG. 3B, a machine learning system may be fed a digital whole slide image of breast tissue, where some of the tissue may possibly be cancerous. A salient tissue detector may filter the image to identify one or more tissue regions that may have cancer, which is a region of interest for identifying the HER2, ER, and/or PR biomarkers that may help guide treatment. Less relevant tissue may be removed, and using the identified salient regions, the trained AI may infer the expression level of each of the HER2, ER, and/or PR biomarkers.

Figure 4A:
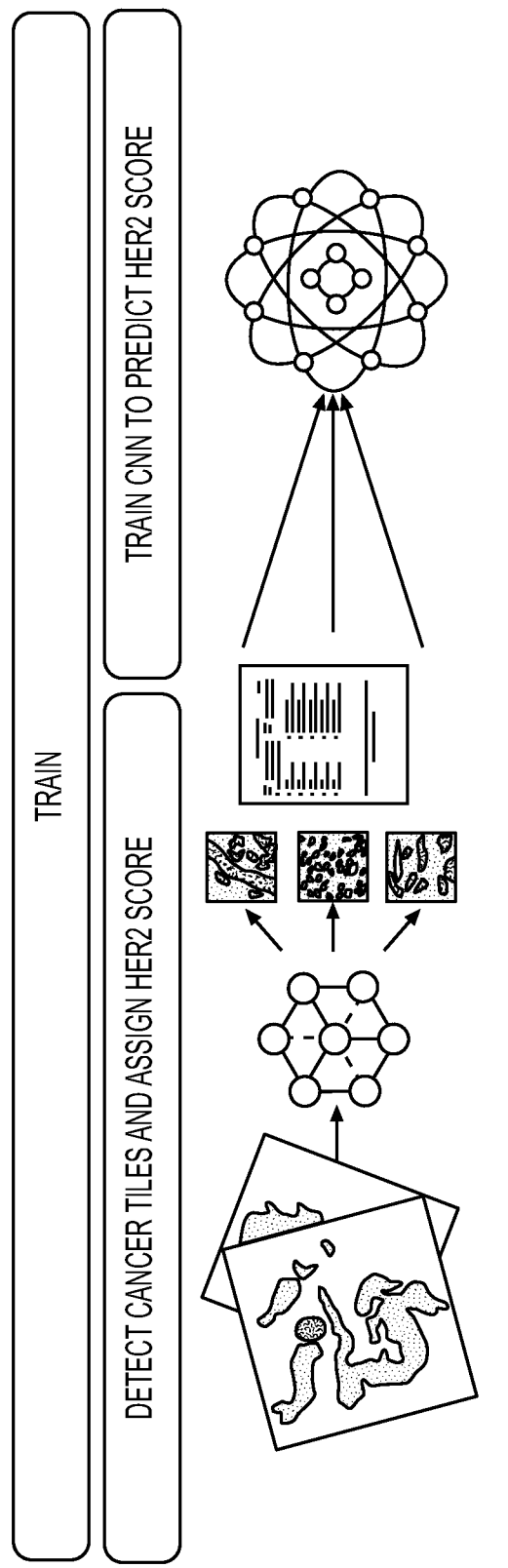
FIGS. 4A to 4U illustrate exemplary systems and methods for predicting HER2 biomarkers by analyzing H&E images, according to one or more exemplary embodiments of the present disclosure.
Figure 4B:
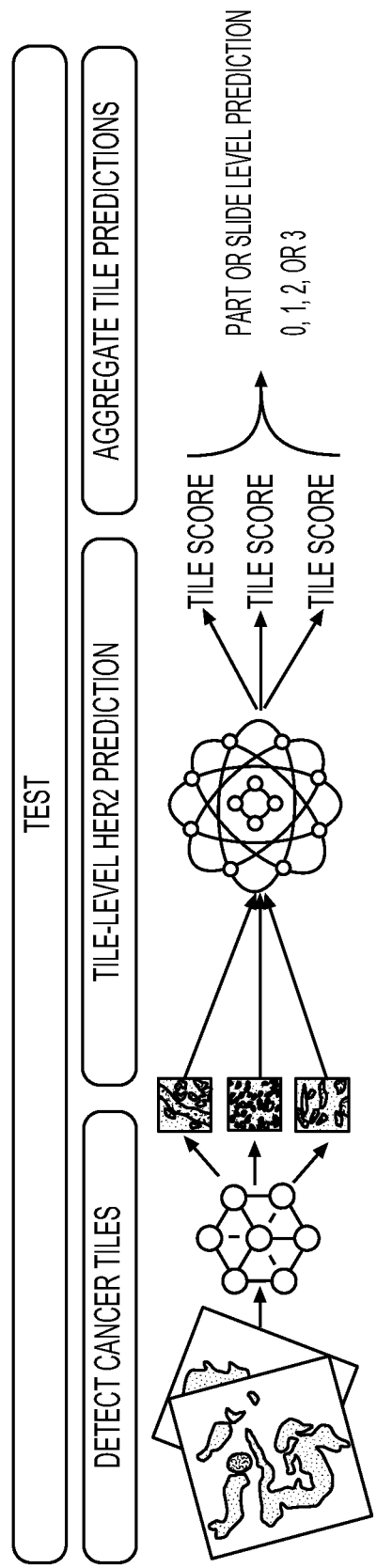
Figure 4C:
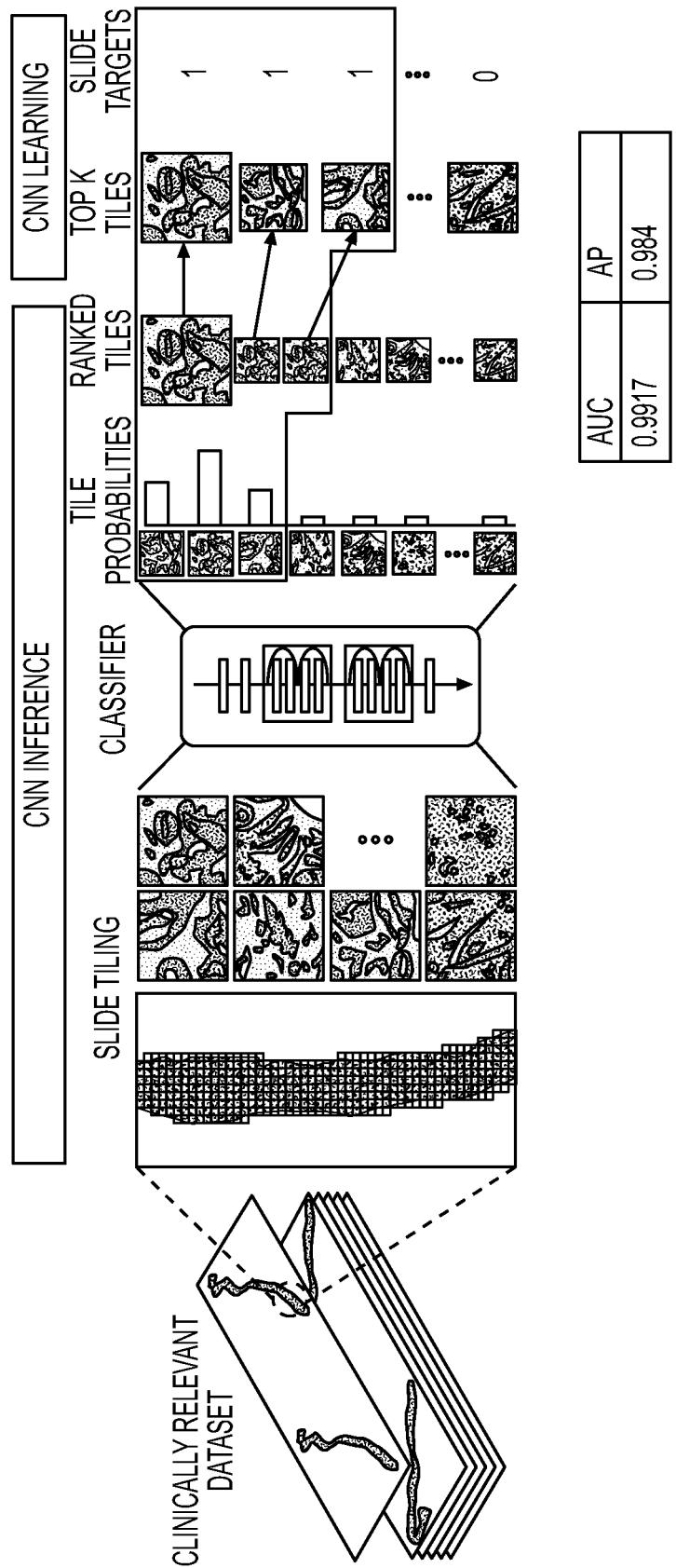
Figure 4D:
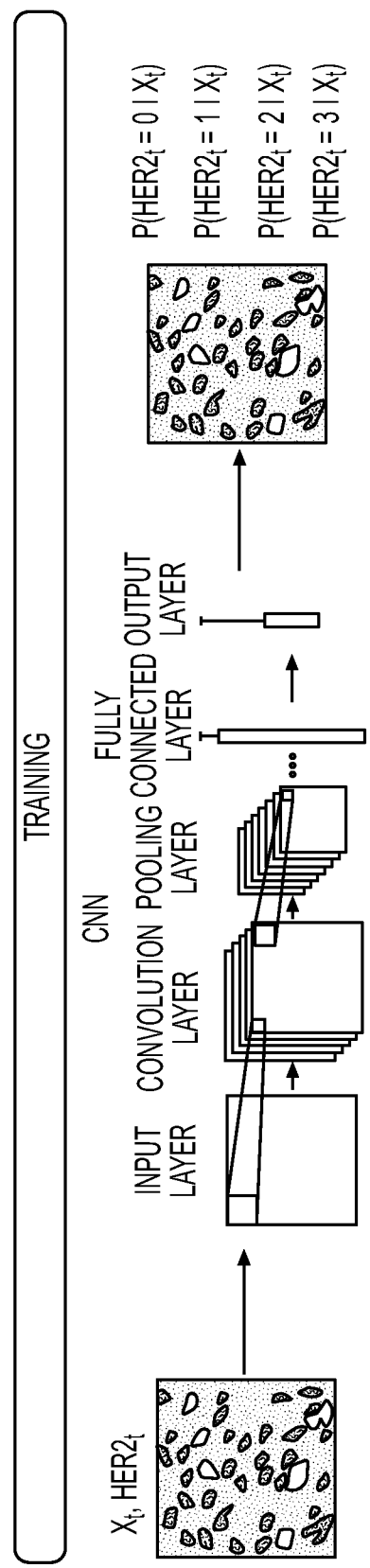
Figure 4E:
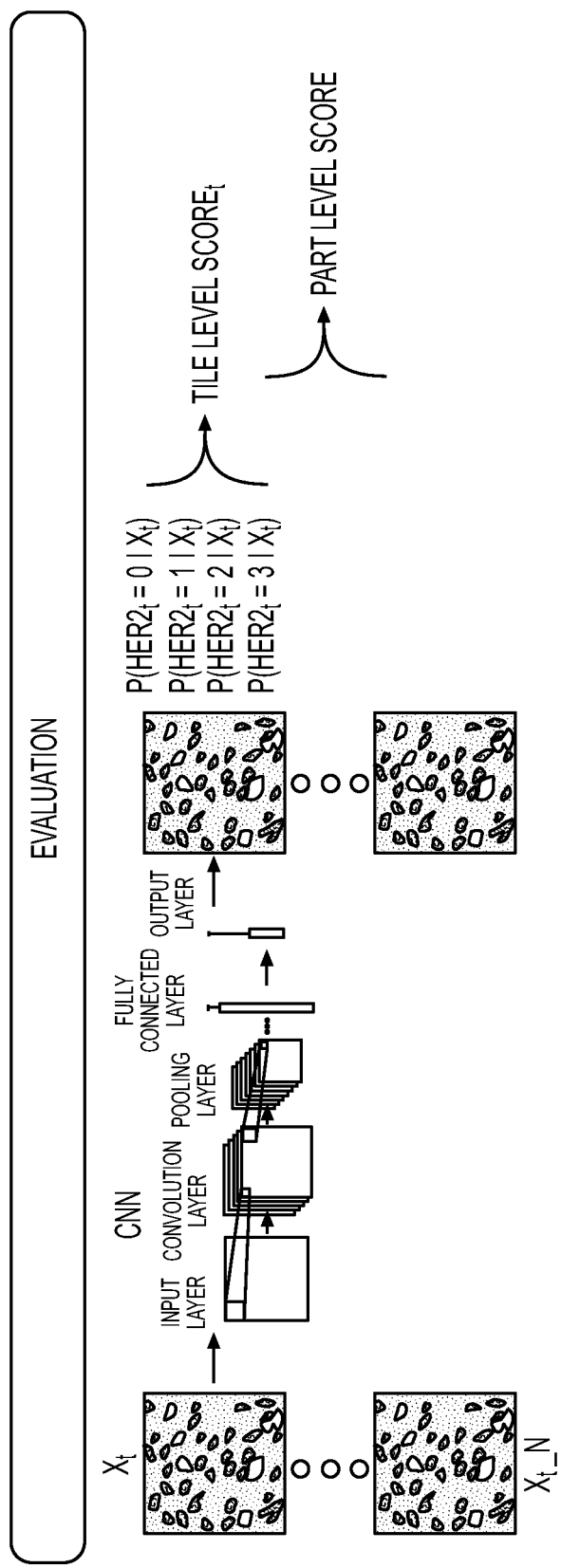
Figure 4G:
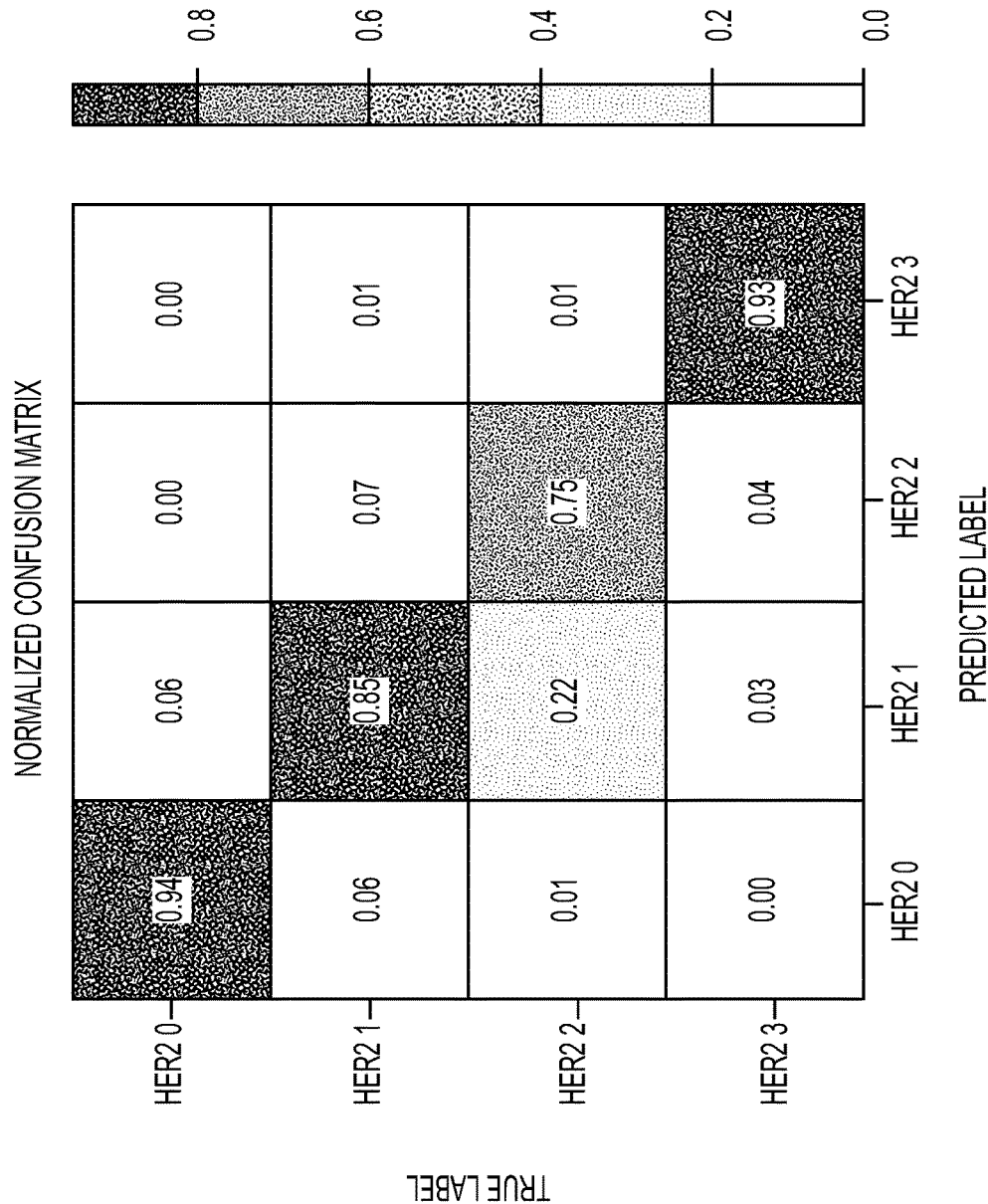
Figures 4H, 4I:
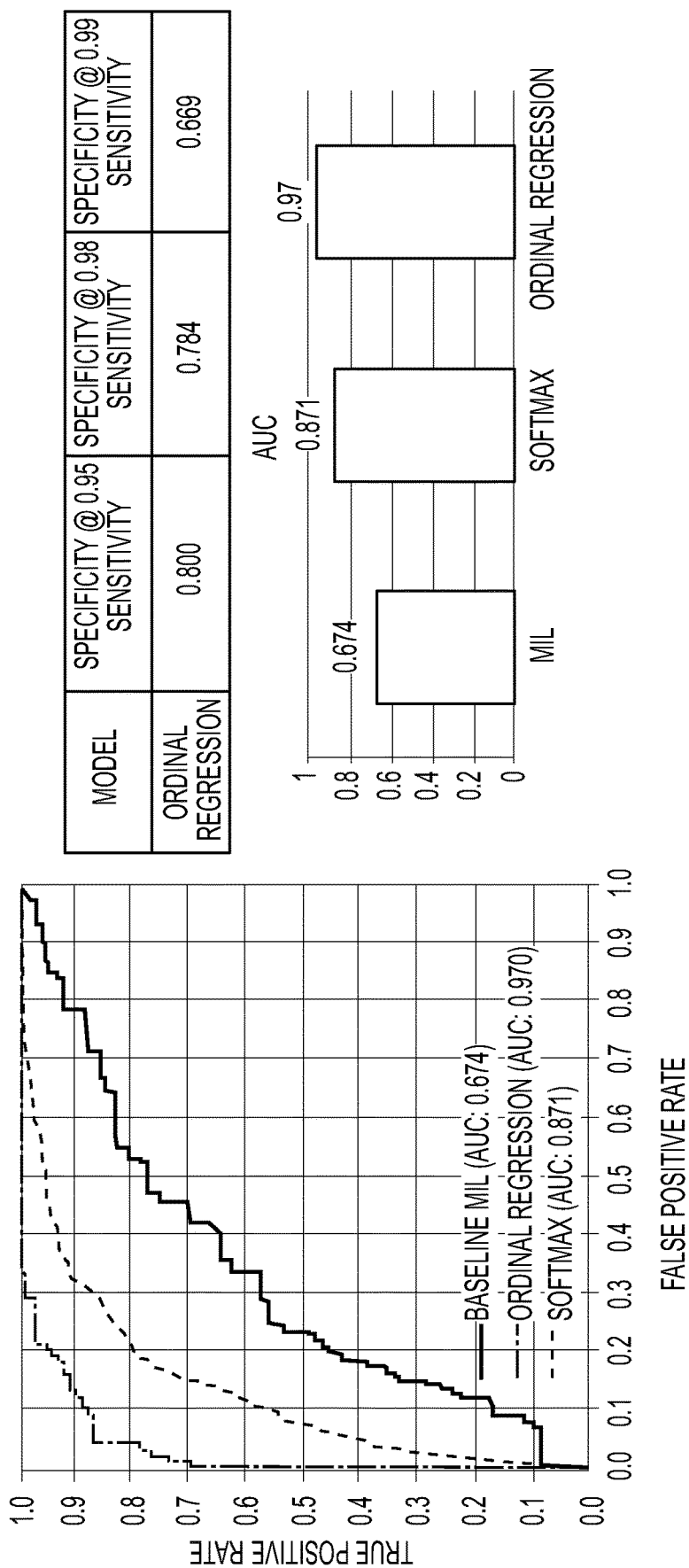
Figure 4M:
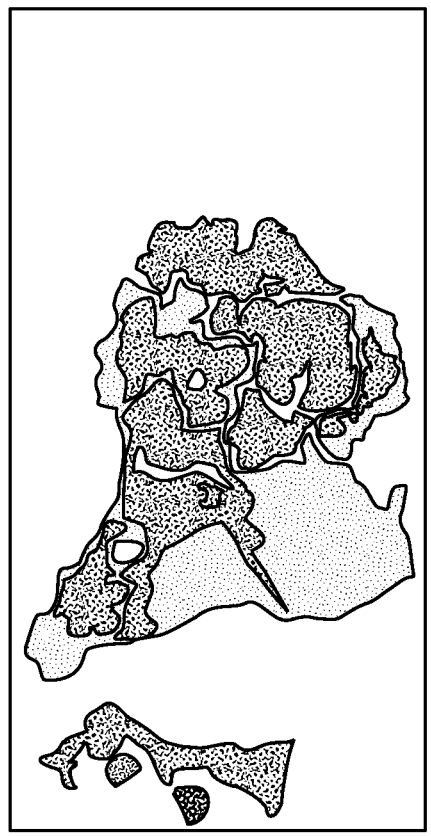
Figure 4L:
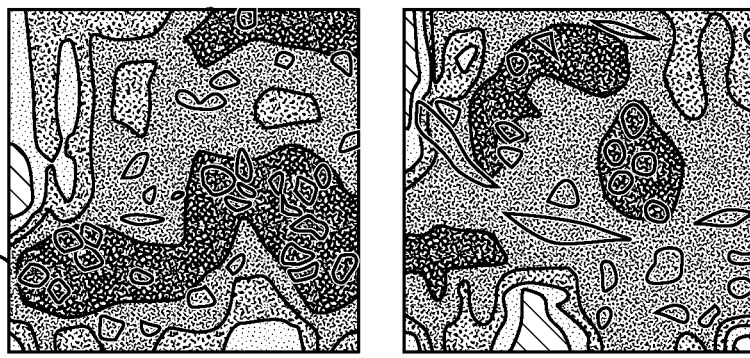
Figure 4L:
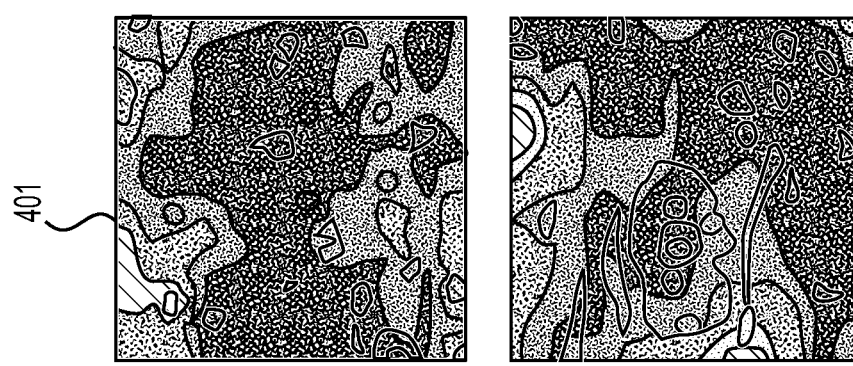
Figure 4O:
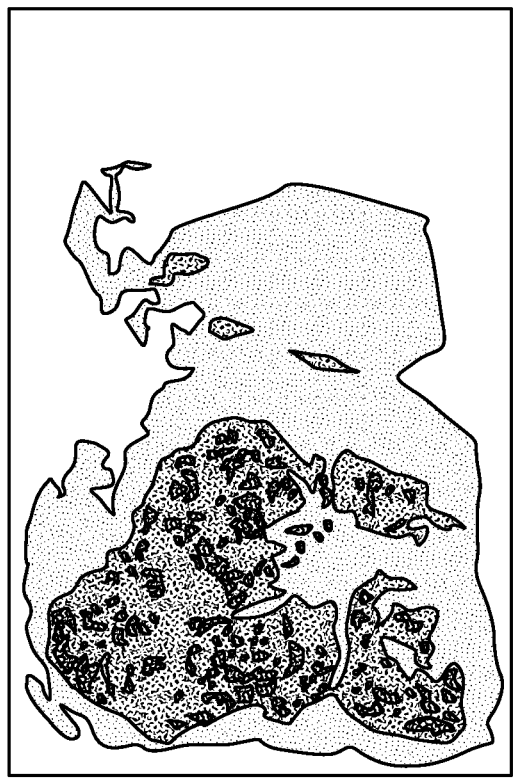
Figure 4N:
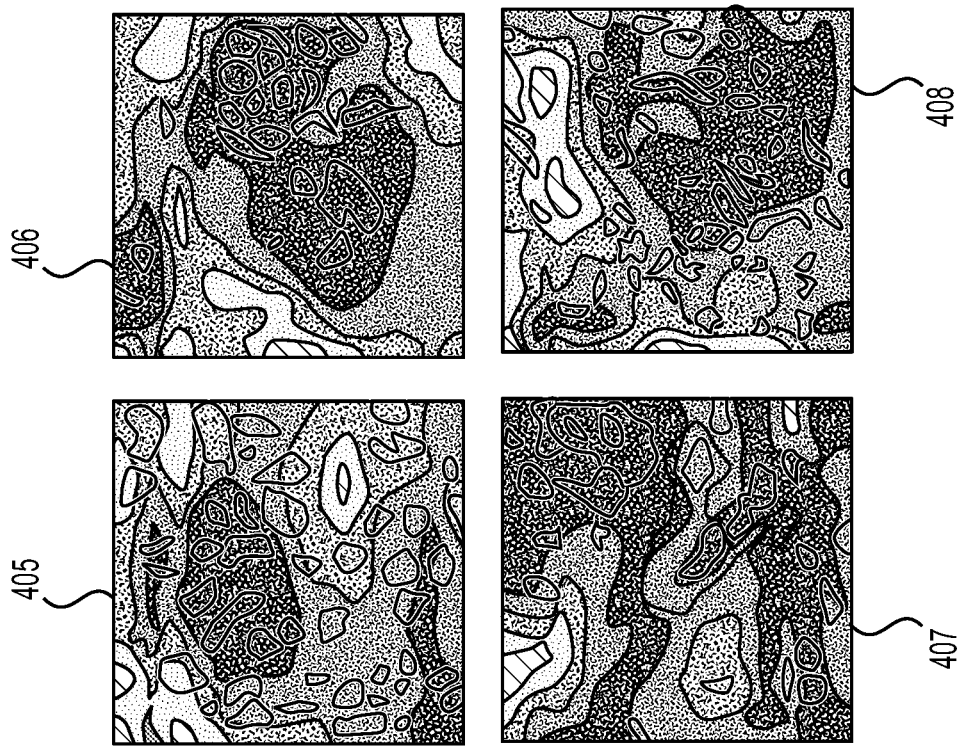
Figure 4Q:
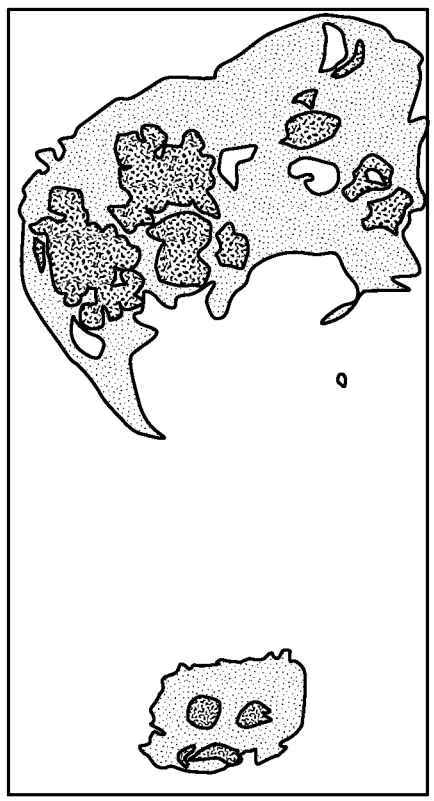
Figure 4P:
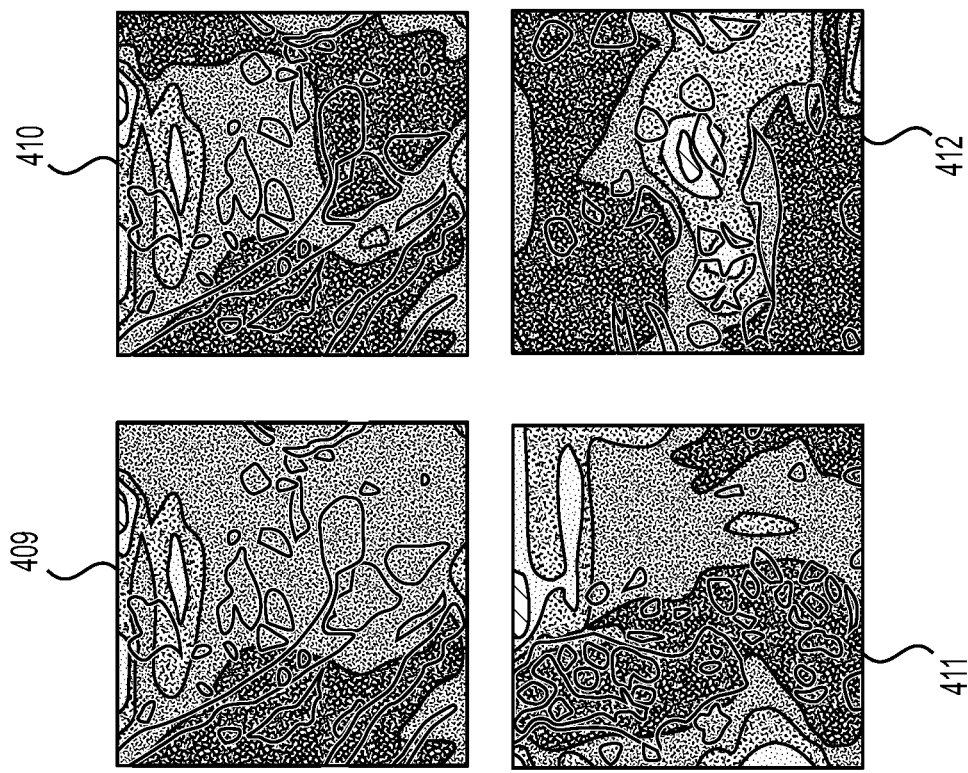
Figure 4S:
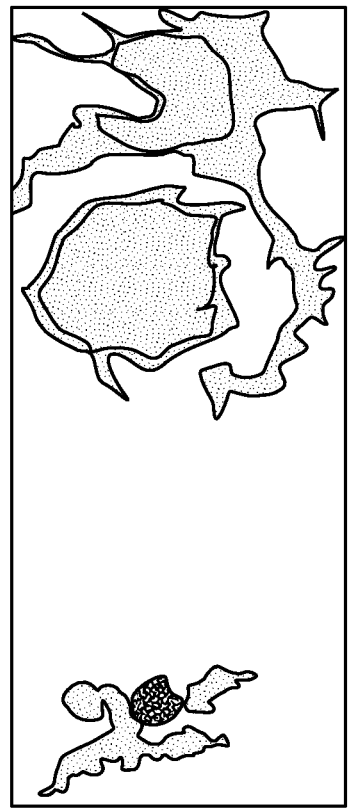
Figure 4R:
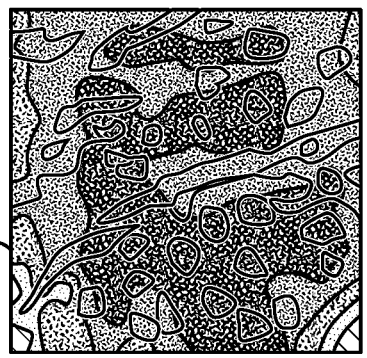
Figure 4R:
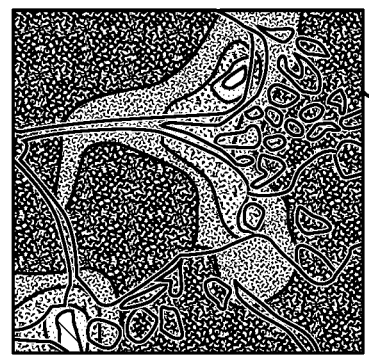
Figure 4R:
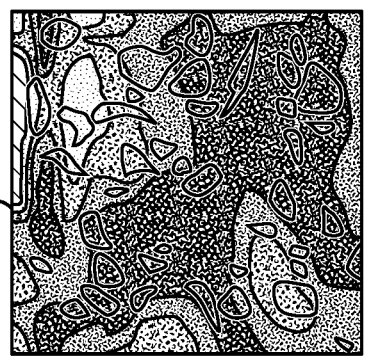
Figure 4R:
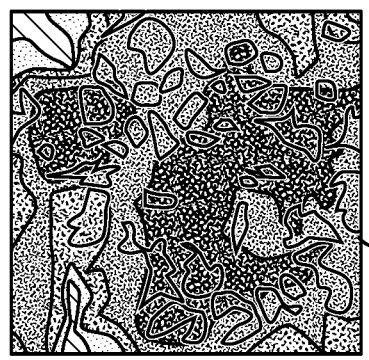
Figure 4U:
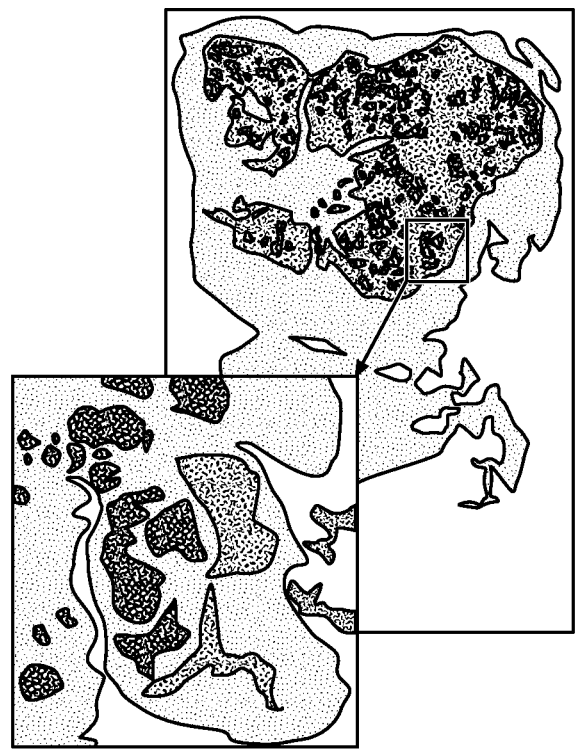

FIGS. 4A to 4U illustrate exemplary systems and methods for predicting HER2 levels from H&E WSI that may possibly have cancer, according to an exemplary embodiment of the present disclosure. For example an input may include all H&E images from a breast cancer part. An exemplary output may be an HER2 score for an expression level. For example, HER2 may be graded using IHC on a scale of 0, 1+, 1+ to 2+, 2+, and/or 3+. Anti-HER2 therapies may be administered based on HER2 expression levels, which may be derived from a likelihood of HER2 being a clonal driver of growth; thus, a tumor may be sensitive to an anti-HER2 antibody, e.g., trastuzumab. However, based on the development of anti-HER2 antibody-drug conjugates (ADCs), which may produce powerful bystander effects, administering anti-HER2 antibodies based on HER2 expression levels might not be the only effective method. Some patients with "low HER2" (e.g., some degree of HER2 expression but insufficient for a tumor to be considered positive by current clinical guidelines) may benefit from anti-HER2 ADCs. However, it may be difficult for biomarkers to define which patients will benefit from these ADCs. An exemplary embodiment of the present disclosure may include an AI-based analysis of histologic and IHC samples of patients enrolled in clinical trials testing ADCs for whom outcome data may be available to characterize the constellation of morphologic features that distinguish: (1) HER2-high from HER2-low; (2) within the HER2-high, patients who responded to ADCs; and/or (3) within the HER2-low, patients who responded to anti-HER2 ADCs. Features employed by the AI algorithms predictive of resistance to these agents may be underpinned by specific repertoires of genetic and/or epigenetic alterations. Exemplary clinical trial data may include digital images of tumors and/or longitudinal follow up information from patients included in anti-HER2 ADC studies.

FIG. 4A illustrates an exemplary training method for predicting an HER2 score from H&E as a 4-way ordinal regression model. For example, a digital image may be broken into sub-regions and tiles of the image may be created. HER2 may be graded using IHC on a scale of 0, 1+, 1+ to 2+, 2+, and/or 3+. The method may include training a CNN to predict the HER2 score. The HER2 score may be from IHC, however, the input may include a set of all H&E images from a part, which may allow for quicker iterations than using weak supervision alone, and may supply the system with more HER2 score information to train from.

FIG. 4B illustrates an exemplary testing method for predicting an HER2 score. For example, a digital image may be broken into sub-regions and tiles of the image may be created. HER2 may be graded using IHC on a scale of 0, 1+, 1+ to 2+, 2+, and/or 3+. The method may include aggregating the tile predictions into a part level HER2 prediction.

FIG. 4C illustrates an exemplary method for detecting tiles with HER2 biomarkers present. For example, a digital image may be broken into sub-regions and tiles of the image may be created. The method may include using classifier training with a CNN to predict a probability that cancer may be present in a tile. The tiles may be ranked based on probabilities and may be used to train a machine learning system which tiles may show invasive cancer and which may be benign. As an example, tiles with a probability of cancer greater than 0.96 may be used to identify invasive cancer versus benign. The AUC number refers to an area under the receiver operating characteristic curve value for the prediction of HER2 scores. The AP number refers to average precision which is the area under a precision-recall curve.

FIG. 4D illustrates an exemplary training method for detecting tiles with HER2 biomarkers present. For example, a digital image may be broken into sub-regions and tiles of the image may be created. The method may include using CNN training to predict 4-way HER2 score predictions (e.g., (P(HER2t=0|Xt), (P(HER2t=0|Xt), (P(HER2t=0|Xt), (P(HER2t=0|Xt))).

FIG. 4E illustrates an exemplary evaluation method for detecting a presence of HER2 biomarkers at a part level. For example, a digital image may be broken into sub-regions and tiles of the image may be created. The method may include using CNN training to predict, at a tile level, a probability of a presence of HER2 biomarkers at a level of 0, 1, 2, or 3. A part level score may be computed, and cancer tiles from the part may be fed into the CNN to get the 4-way HER2 score predictions. The predictions may be aggregated across all tiles to do the classification.

FIG. 4F illustrates an exemplary dataset related to an exemplary training set and a test set for detecting parts and/or tiles with HER2 biomarkers present. For the data in FIG. 4F, non-invasive tiles have been removed. Thus, the dataset includes tiles classified as invasive carcinoma by the detection model. The right side of FIG. 4F illustrates that HER2 biomarkers at a level of 0 and 1+ may be considered negative, scores of 3+ may be considered positive, and scores of 1+ to 2+ and 2+ may be considered equivocal, and may be removed from the dataset.

FIG. 4G illustrates an exemplary normalized confusion matrix for an exemplary dataset. Three tasks may be performed for the data: (1) multi-way classification; (2) detecting HER2 greater than zero from H&E; and/or (detecting HER2− vs HER2+ from H&E. The numbers in the exemplary matrix represent a predicted label versus the true label for HER2 levels of 0, 1, 2, and/or 3. The legend on the right highlights an accuracy level for each of the predictions.

FIG. 4H illustrates an exemplary graph that charts a false positive rate vs. a true positive rate for HER2 level 0 vs. HER2 level 1, 2, and 3 (e.g., score=$\max_t(P(HER2>0|X_t))$). The baseline MIL model indicates an AUC of 0.674. The ordinal regression model indicates an AUC of 0.970. The softmax model indicates an AUC of 0.871.

FIG. 4I illustrates another exemplary graph for HER2 level 0 vs. HER2 level 1, 2, and/or 3 (e.g., score=$\max_t(P(HER2>0|X_t))$), with the AUCs for the MIL, softmax, and/or ordinal regression models. Additionally, FIG. 4I illustrates a specificity value for ordinal regression model at a 0.95 sensitivity, a 0.98 sensitivity, and a 0.669 sensitivity.

FIG. 4J illustrates an exemplary graph that charts a false positive rate vs. a true positive rate for HER2 Negative (0/1) vs. HER2 Positive (3) (e.g., score=$\max_t(P(HER2=3|X_t))$). The data set excludes HER2 scores of 2. The baseline MIL model indicates an AUC of 0.804. The ordinal regression model indicates an AUC of 0.978. The softmax model indicates an AUC of 0.939.

FIG. 4K illustrates another exemplary graph for HER2 Negative (0/1) vs. HER2 Positive (3) (e.g., score=$\max_t(P(HER2=3|X_t))$), with the AUCs for the MIL, softmax, and/or ordinal regression models. Additionally, FIG. 4I illustrates a specificity value for ordinal regression model at a 0.95 sensitivity, a 0.98 sensitivity, and a 0.669 sensitivity.

FIG. 4L illustrates exemplary visualizations for H&E tiles correctly predicted as HER2 level 0. For example, H&E tiles with heat maps 401, 402, 403, 404 were correctly predicted by the biomarker tool as having HER2 level 0.

FIG. 4M illustrates an exemplary IHC stain of a same part as the tiles illustrated in FIG. 4L.

FIG. FIG. 4N illustrates exemplary visualizations for H&E tiles predicted as HER2 level 3. For example, H&E tiles with heat maps 405, 406, and 408 were correctly predicted by the biomarker tool as having HER2 level 3. H&E tile 407 was predicted as having HER2 level 1.

FIG. 4O illustrates an exemplary IHC stain of a same part as the tiles illustrated in FIG. 4N.

FIG. 4P illustrates exemplary visualizations for H&E tiles correctly predicted as HER2 level 1. For example, H&E tiles with heat maps 409, 410, 411, 412 were correctly predicted by the biomarker tool as having HER2 level 1.

FIG. 4Q illustrates an exemplary IHC stain of a same part as the tiles illustrated in FIG. 4P.

FIG. 4R illustrates exemplary visualizations for H&E tiles incorrectly predicted as HER2 level 2. For example, H&E tiles with heat maps 413 and 414 were incorrectly predicted as HER2 level 2, and H&E tiles 415 and 416 were predicted as HER2 level 0.

FIG. 4S illustrates an exemplary IHC stain of a same part as the tiles illustrated in FIG. 4R.

Figure 4T:
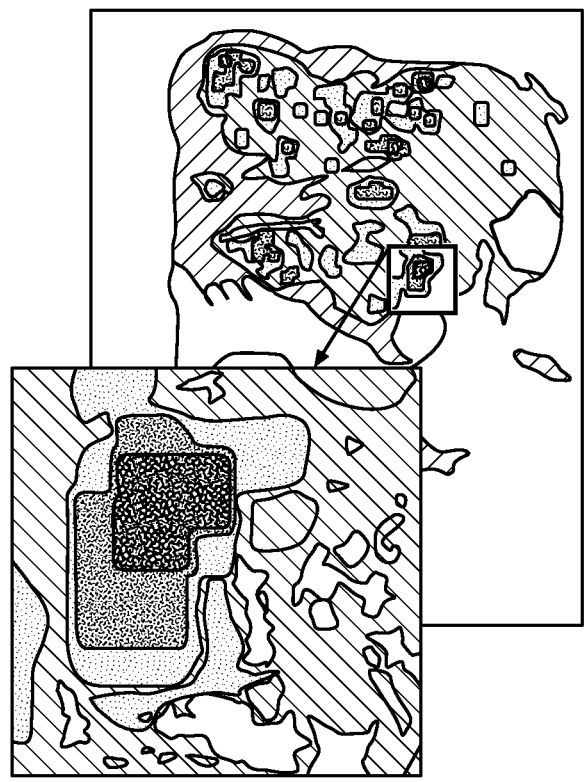

FIG. 4T illustrates an exemplary H&E heatmap in which the slide was correctly classified as HER2+.

FIG. 4U illustrates an exemplary IHC stain in which the slide was correctly classified as HER2+.

Figure 5:
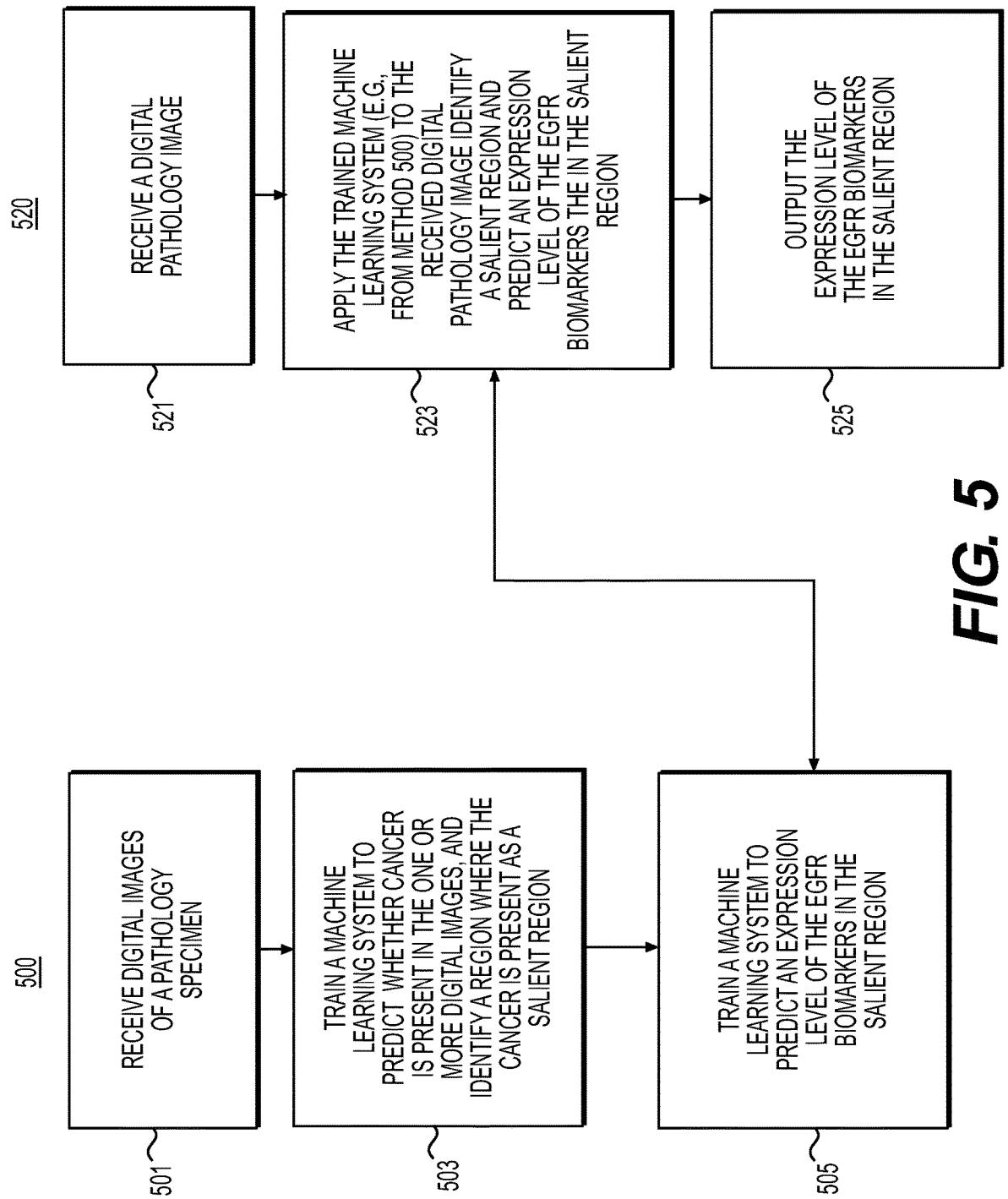
FIG. 5 is a flowchart illustrating an exemplary method for predicting epithelial growth factor receptor (EGFR) biomarkers, according to an exemplary embodiment of the present disclosure.

As illustrated in FIG. 5, according to one embodiment, exemplary methods 500 and 520 for predicting epithelial growth factor receptor (EGFR) biomarkers are described below.

Lung cancers that harbor EGFR activating gene mutations may enable treatments with specialized drugs that may improve outcome. About 15% of people with lung cancer in the United States harbor an EGFR mutation, but for people of East Asian descent with lung cancer, up to 50% are estimated to have targetable alterations affecting this gene. EGFR mutations may be determined by a number of sequencing methods. Techniques presented herein may define a presence of EGFR activating mutation and/or EGFR mutations that cause resistance to anti-EGFR agents (e.g. EGFR T790m mutation) from H&E stained lung tissue specimens.

Exemplary methods 500 and 520 for predicting EGFR biomarkers may include one or more of the steps below. In step 501, during a training phase, the method may include receiving one or more digital images of a lung tissue specimen stained with H&E into a digital storage device (e.g., hard drive, network drive, cloud storage, RAM, etc.), and/or receiving, for one or more images, an indication of the presence or absence of the salient region, e.g., cancerous tissue. One or more digital images may be broken into sub-regions and the saliency of one or more sub-regions may be determined. Regions may be specified in a variety of methods, including creating tiles of the image, segmentations based edge/contrast, segmentations via color differences, supervised determination by the machine learning system, and/or EdgeBoxes, etc.

In step 503, the method may include training a machine learning algorithm that takes, as input, a digital image of a pathology specimen stained with H&E and predicting whether a salient region exists, e.g., whether cancer is possibly present, using an AI-based method and/or manual specification. The machine learning algorithm may be performed in a weakly-supervised or strongly-supervised manner.

In step 505, the method may include training the machine learning algorithm to predict an expression level of one or more of the EGFR biomarkers based on the salient regions of the digital image of the pathology specimen and the received biomarker/score information. The method may include receiving an indication for each slide of the presence of one or more of the EGFR mutation. The presence of the biomarker may be identified using validated sequencing methods. The presence of the mutation may be reported as a categorical variable. The mutation's variant allele fraction and cancer cell fraction (e.g., the bioinformatically-inferred percentage of cancer cells in a sample harboring a given mutation) may be reported on a numeric, ordinal, or binary scale. The indication may be assigned to the entire image and/or image sub-regions.

According to one embodiment, an exemplary method 520 for using the biomarker tool to predict EGFR biomarkers may include one or more of the steps below. In step 521, the method may include receiving one or more digital images of an H&E stained pathology specimen (e.g., breast cancer pathology specimen) into a digital storage device (e.g., hard drive, network drive, cloud storage, RAM, etc.). In step 523, the method may include applying the salient region detector machine learning algorithm (e.g., method 500 (e.g., deep neural network)) to the image to predict if cancer is possibly present in the received images and to identify salient image regions that may correspond to cancerous tissue using an AI-based method and/or manual specification. Additionally, the method may include applying the machine learning biomarker detection algorithm (e.g., method 500) to the image to determine a prediction of a presence of an EGFR mutation. The method may include assigning a presence of an EGFR mutation to a diagnostic category.

In step 525, the method may include outputting the prediction to an electronic storage device. The method may include displaying a visual indicator to alert the user (e.g., a pathologist, histology technician, etc.) of the expression levels of one or more biomarkers.

Figure 6:
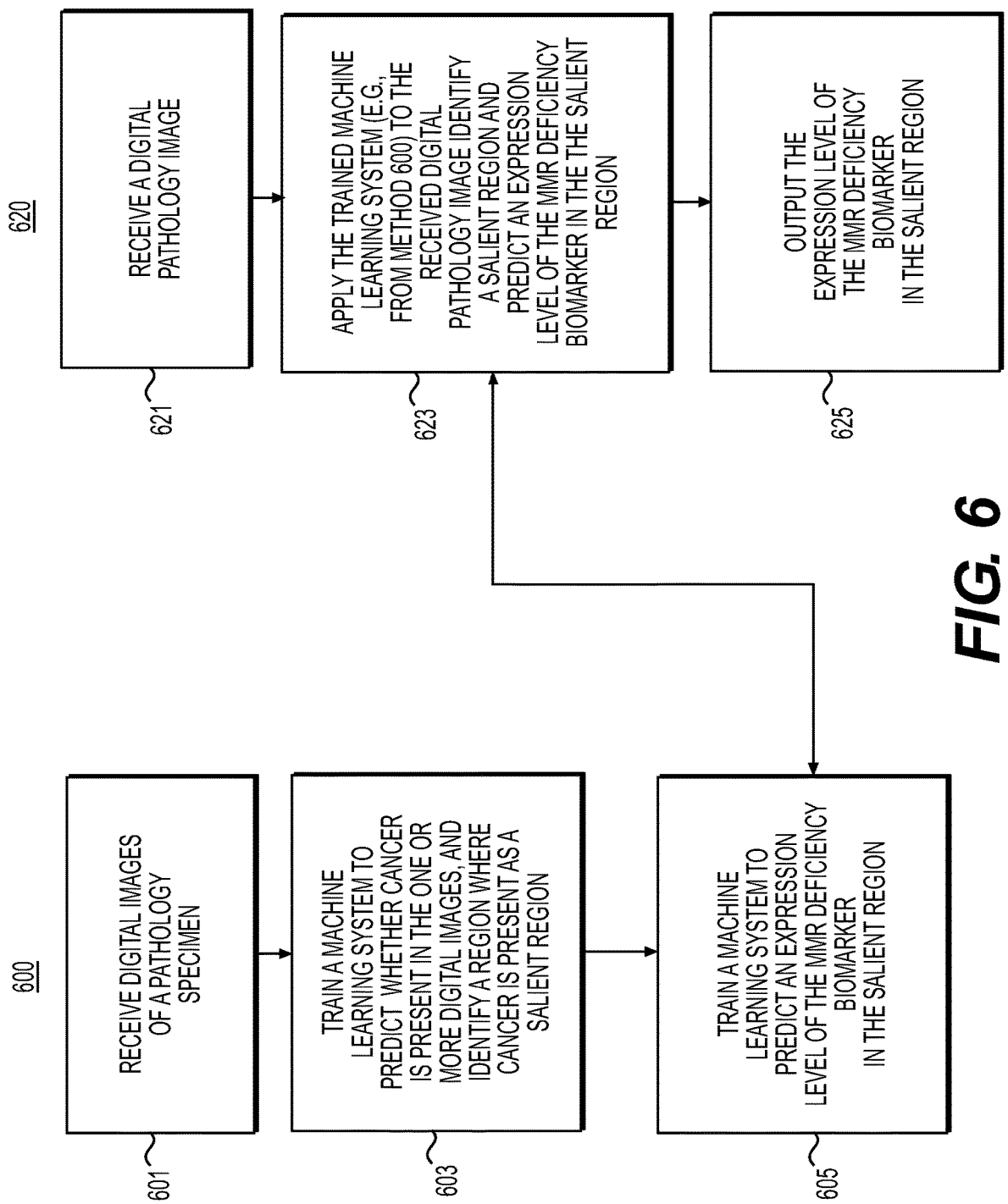
FIG. 6 is a flowchart illustrating an exemplary method for predicting DNA Mismatch Repair (MMR) deficiency biomarkers, according to an exemplary embodiment of the present disclosure.

As illustrated in FIG. 6, according to one embodiment, exemplary methods 600 and 620 for predicting DNA Mismatch Repair (MMR) deficiency biomarkers are described below.

MMR genes may help identify metastatic cancer patients who may benefit from immunotherapy. Although all patients with metastatic disease may be candidates for immunotherapy, as a presence of MMR deficiency and/or high levels of microsatellite instability (MSI-H) predict response to immunotherapy in a tissue agnostic basis, screening for MMR may be important. In one embodiment, MMR deficiency and/or MSI-H may be detected from H&E images, without a need of IHC for MMR protein level assessment and/or PCR or massively parallel sequencing for the assessment of MSI-H.

Exemplary methods 600 and 620 for predicting DNA Mismatch Repair (MMR) deficiency biomarkers may include one or more of the steps below. In step 601, during a training phase, the method may include receiving one or more digital images of a tissue specimen stained with H&E into a digital storage device (e.g., hard drive, network drive, cloud storage, RAM, etc.), receiving, for one or more images, an indication of the presence or absence of the salient region, e.g., cancerous tissue, and/or receiving an indication of the type of tissue in the tissue specimen. One or more digital images may be broken into sub-regions and the saliency of one or more sub-regions may be determined. Regions may be specified in a variety of methods, including creating tiles of the image, segmentations based edge/contrast, segmentations via color differences, supervised determination by the machine learning system, and/or Edge-Boxes, etc.

In step 603, the method may include training a machine learning algorithm that takes, as input, a digital image of a pathology specimen stained with H&E and predicting whether a salient region exists, e.g., whether cancer is possibly present, using an AI-based method and/or manual specification. The machine learning algorithm may be performed in a weakly-supervised or strongly-supervised manner.

In step 605, the method may include training the machine learning algorithm to predict an expression level of one or more of the MMR deficiency biomarkers based on the salient regions of the digital image of the pathology specimen and the received biomarker/score information. The method may include receiving an indication, for each slide, of the MMR deficiency level. The indication may be obtained via IHC, and/or the presence of MSI-H as defined by PCR, or massively parallel sequencing. The level of expression may be on a numeric, ordinal, or binary scale. The indication may be assigned to the entire image and/or image sub-regions.

According to one embodiment, an exemplary method 620 for using the biomarker tool to predict MMR deficiency biomarkers may include one or more of the steps below. In step 621, the method may include receiving one or more digital images of an H&E stained pathology specimen into a digital storage device (e.g., hard drive, network drive, cloud storage, RAM, etc.). In step 623, the method may include applying the salient region detector machine learning algorithm (e.g., method 600 (e.g., deep neural network)) to the image to predict if cancer is possibly present in the received images and to identify salient image regions that may correspond to cancerous tissue using an AI-based method and/or manual specification. Additionally, the method may include applying the machine learning biomarker detection algorithm (e.g., method 600) to the image to determine a prediction of expression levels of MMR proteins, MMR deficiency, and/or MSI-H. The method may include assigning expression levels of MMR proteins, MMR deficiency, and/or MSI-H to a diagnostic category.

In step 625, the method may include outputting the prediction to an electronic storage device. The method may include displaying a visual indicator to alert the user (e.g., a pathologist, histology technician, etc.) of the expression levels of one or more biomarkers.

Figure 7:
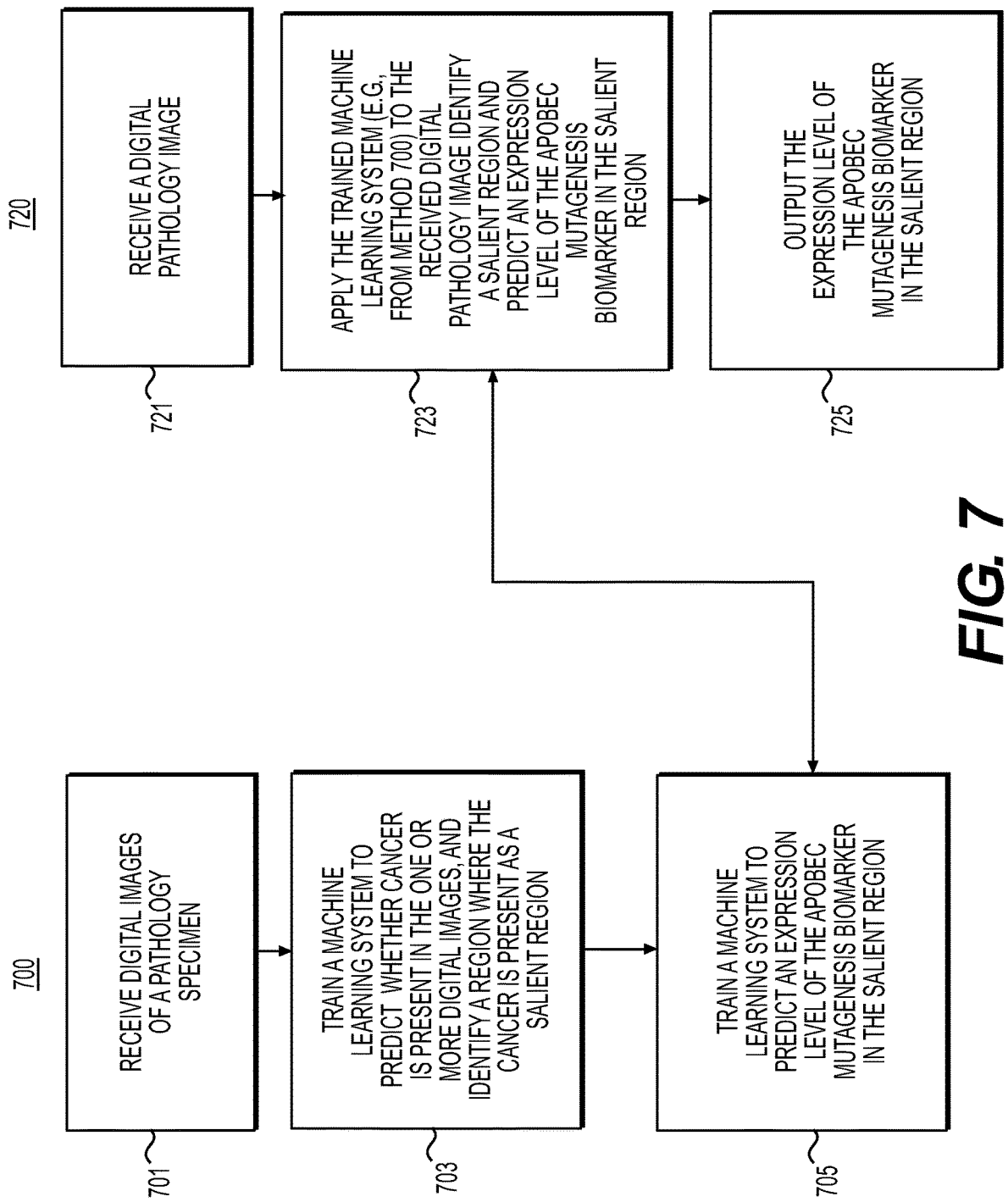
FIG. 7 is a flowchart illustrating an exemplary method for predicting APOBEC mutagenesis biomarkers, according to an exemplary embodiment of the present disclosure.

As illustrated in FIG. 7, according to one embodiment, exemplary methods 700 and 720 for predicting APOBEC mutagenesis biomarkers are described below.

APOBEC cytidine deaminases may induce mutation clusters in human tumors. The APOBEC mutagenesis process may be prevalent across cancer types, for example, in primary bladder cancers, post-treatment ER-positive breast cancers, and/or lung cancers. APOBEC mutagenesis may be identified in cancers through sequencing analysis of the tumors. Techniques presented herein may be used to detect APOBEC mutagenesis.

Exemplary methods 700 and 720 for predicting APOBEC mutagenesis biomarkers may include one or more of the steps below. In step 701, during a training phase, the method may include receiving one or more digital images of a tissue specimen stained with H&E into a digital storage device (e.g., hard drive, network drive, cloud storage, RAM, etc.), receiving, for one or more images, an indication of the presence or absence of the salient region, e.g., cancerous tissue, and/or receiving a tissue specimen type. One or more digital images may be broken into sub-regions and the saliency of one or more sub-regions may be determined. Regions may be specified in a variety of methods, including creating tiles of the image, segmentations based edge/contrast, segmentations via color differences, supervised determination by the machine learning system, and/or Edge-Boxes, etc.

In step 703, the method may include training a machine learning algorithm that takes, as input, a digital image of a pathology specimen, and predicts whether a salient region exists, e.g., whether cancer is possibly present, based on the tissue specimen type, using an AI-based method and/or manual specification. The machine learning algorithm may be performed in a weakly-supervised or strongly-supervised manner.

In step 705, the method may include training the machine learning algorithm to predict an expression level of one or more of the APOBEC mutagenesis biomarkers based on the salient regions of the digital image of the pathology specimen and/or the received biomarker/score information. The method may include receiving an indication for each slide of the APOBEC mutagenesis biomarker level. The level may be on a numeric, ordinal, or binary scale. The indication may be assigned to the entire image and/or image sub-regions.

According to one embodiment, an exemplary method 720 for using the biomarker tool to predict APOBEC mutagenesis biomarkers may include one or more of the steps below. In step 721, the method may include receiving one or more digital images of a pathology specimen into a digital storage device (e.g., hard drive, network drive, cloud storage, RAM, etc.). In step 723, the method may include applying the salient region detector machine learning algorithm (e.g., method 700 (e.g., deep neural network)) to the image to predict if cancer is possibly present in the received images and to identify salient image regions that may correspond to cancerous tissue using an AI-based method and/or manual specification. Additionally, the method may include applying the machine learning biomarker detection algorithm (e.g., method 700) to the image to determine a prediction of an APOBEC mutagenesis biomarker level. The method may include the APOBEC mutagenesis biomarker level to a diagnostic category.

In step 725, the method may include outputting the prediction to an electronic storage device. The method may include displaying a visual indicator to alert the user (e.g., a pathologist, histology technician, etc.) of the expression levels of one or more biomarkers.

Figure 8:
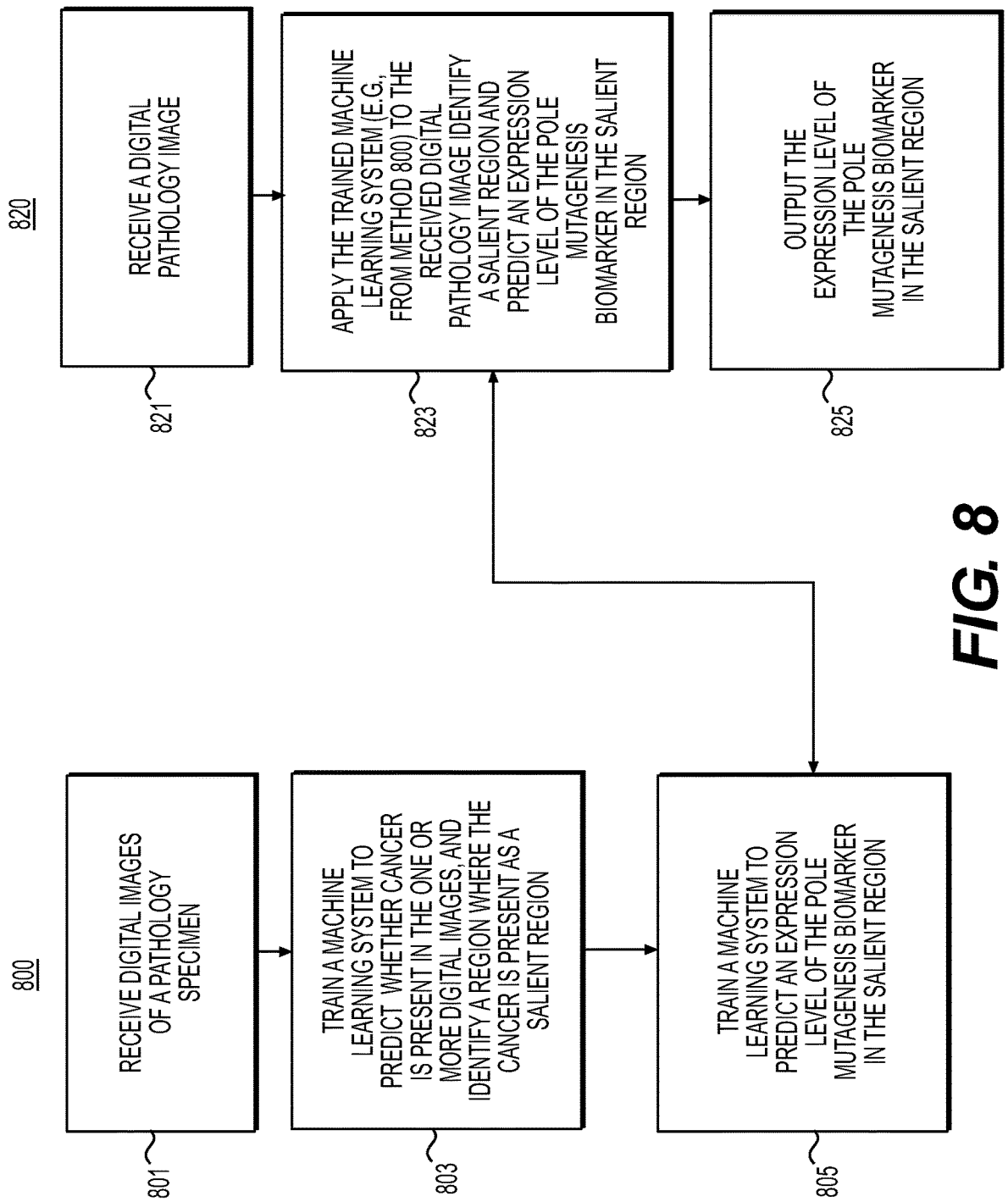
FIG. 8 is a flowchart illustrating an exemplary method for predicting DNA polymerase ε (POLE) mutagenesis biomarkers, according to an exemplary embodiment of the present disclosure.

As illustrated in FIG. 8, according to one embodiment, exemplary methods 800 and 820 for predicting DNA polymerase ε (POLE) mutagenesis biomarkers are described below.

Defective DNA POLE proofreading may lead to an ultra-mutator phenotype in cancers, characterized by extensive somatic single nucleotide polymorphism mutations. POLE mutations and their associated ultra-mutator phenotype may be predictive of response to immune-checkpoint inhibitors. Techniques presented herein may be used to detect POLE mutagenesis in cancer, and may use detected POLE mutagenesis as a biomarker of response to immune-checkpoint inhibitors.

Exemplary methods 800 and 820 for predicting POLE mutagenesis biomarkers may include one or more of the steps below. In step 801, during a training phase, the method may include receiving one or more digital images of a tissue specimen stained with H&E into a digital storage device (e.g., hard drive, network drive, cloud storage, RAM, etc.), receiving, for one or more images, an indication of the presence or absence of the salient region, e.g., cancerous tissue, and/or receiving an indication of a tissue specimen type. One or more digital images may be broken into sub-regions and the saliency of one or more sub-regions may be determined. Regions may be specified in a variety of methods, including creating tiles of the image, segmentations based edge/contrast, segmentations via color differences, supervised determination by the machine learning system, and/or EdgeBoxes, etc.

In step 803, the method may include training a machine learning algorithm that takes, as input, a digital image of a pathology specimen, and predicts whether a salient region exists, e.g., whether cancer is possibly present, based on the indications, using an AI-based method and/or manual specification. The machine learning algorithm may be performed in a weakly-supervised or strongly-supervised manner.

In step 805, the method may include training the machine learning algorithm to predict an expression level of one or more of the POLE mutagenesis biomarkers based on the salient regions of the digital image of the pathology specimen and/or the received biomarker/score information. The method may include receiving an indication of the presence of POLE mutations (e.g., categorical), their variant allele (e.g., numerical) and cancer cell fractions (e.g., numerical), and the presence (e.g., categorical) and abundance (e.g., numerical) for the POLE mutagenesis process. The level of expression may be on a numeric, ordinal, or binary scale. The indication may be assigned to the entire image and/or image sub-regions.

According to one embodiment, an exemplary method 820 for using the biomarker tool to predict POLE mutagenesis biomarkers may include one or more of the steps below. In step 821, the method may include receiving one or more digital images of a pathology specimen into a digital storage device (e.g., hard drive, network drive, cloud storage, RAM, etc.). In step 823, the method may include applying the salient region detector machine learning algorithm (e.g., method 800 (e.g., deep neural network)) to the image to predict if cancer is possibly present in the received images and/or to identify salient image regions that may correspond to cancerous tissue using an AI-based method and/or manual specification. Additionally, the method may include applying the machine learning biomarker detection algorithm (e.g., method 800) to the image to determine a prediction of a presence of a POLE mutation, its variant allele fraction and cancer cell fraction, and the level of POLE mutagenesis. The method may include assigning the presence of a POLE mutation, its variant allele fraction and cancer cell fraction, and the level of POLE mutagenesis to a diagnostic category.

In step 825, the method may include outputting the prediction to an electronic storage device. The method may include displaying a visual indicator to alert the user (e.g., a pathologist, histology technician, etc.) of the expression levels of one or more biomarkers.

Figure 9:
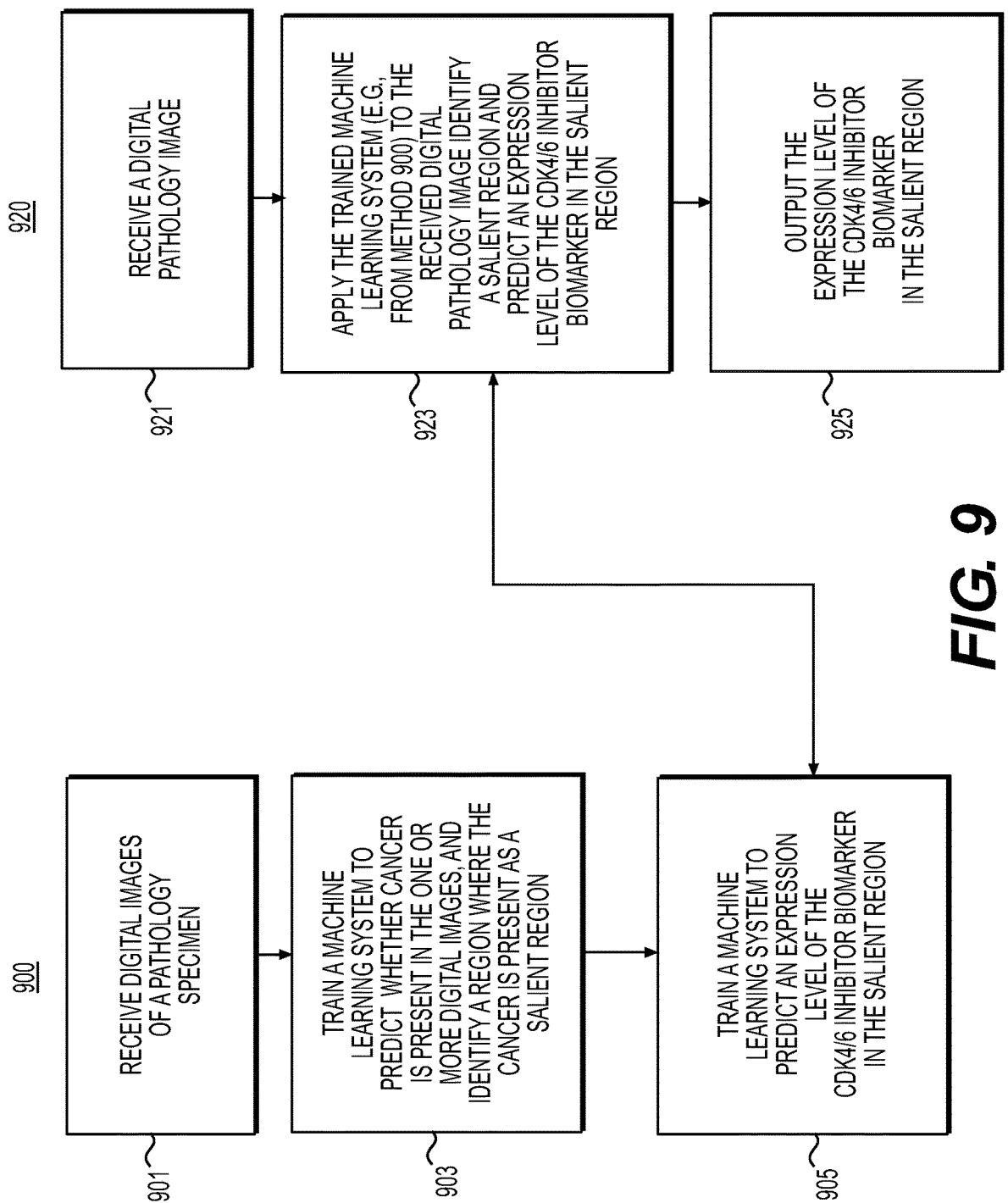
FIG. 9 is a flowchart illustrating an exemplary method for predicting CDK4/6 inhibitor biomarkers, according to an exemplary embodiment of the present disclosure.

As illustrated in FIG. 9, according to one embodiment, exemplary methods 900 and 920 for predicting CDK4/6 inhibitor biomarkers are described below.

CDK4/6 inhibitors may be a class of drugs that target the CDK4 and CDK6 enzymes. CDK4/6 enzymes may be useful in cell division, and drugs that act as CDK4/6 inhibitors may be used to treat cancers, including ER-positive breast cancer. Determining whether a cancer is resistant to CDK4/6 inhibitor may help guide treatment so that unnecessary drugs are not given to a patient. Techniques presented herein may be used to detect if a tumor that is known to be ER-positive is resistant to CDK4/6 inhibitors. The ER-positive determination may be performed using a technique such as IHC, and/or may be determined using another method described herein.

Exemplary methods 900 and 920 for predicting CDK4/6 inhibitor biomarkers may include one or more of the steps below. In step 901, during a training phase, the method may include receiving one or more digital images of a tissue specimen stained with H&E into a digital storage device (e.g., hard drive, network drive, cloud storage, RAM, etc.), identifying salient image regions that correspond to cancerous tissue using an AI-based method and/or manual specification, and/or receiving an indication for one or more images of the CDK4/6 inhibitor biomarker level. The level of expression may be on a numeric, ordinal, or binary scale. The indication may be assigned to the entire image and/or image sub-regions. Salient regions may be identified as having cancer and/or being estrogen receptor (ER) positive.

In step 903, the method may include training a machine learning algorithm that takes, as input, a digital image of a pathology specimen, and predicts whether a salient region exists, e.g., whether cancer is possibly present, based on the indications, using an AI-based method and/or manual specification. The machine learning algorithm may be performed in a weakly-supervised or strongly-supervised manner.

In step 905, the method may include training the machine learning algorithm to predict an expression level of one or more of the CDK4/6 inhibitor biomarkers based on the salient regions of the digital image of the pathology specimen and/or the received biomarker/score information.

According to one embodiment, an exemplary method 920 for using the biomarker tool to predict CDK4/6 inhibitor biomarkers may include one or more of the steps below. In step 921, the method may include receiving one or more digital images of a pathology specimen into a digital storage device (e.g., hard drive, network drive, cloud storage, RAM, etc.). In step 923, the method may include applying the salient region detector machine learning algorithm (e.g., method 900) to the image to predict if cancer is possibly present in the received images and/or to identify salient image regions that may correspond to cancerous tissue using an AI-based method and/or manual specification. Additionally, the method may include applying the machine learning biomarker detection algorithm (e.g., method 900) to the image to determine a prediction of whether a tumor is resistant to CDK4/6 inhibition. The method may include assigning a level of resistance to CDK4/6 inhibition to a diagnostic category.

In step 925, the method may include outputting the prediction to an electronic storage device. The method may include displaying a visual indicator to alert the user (e.g., a pathologist, histology technician, etc.) of the expression levels of one or more biomarkers.

Figure 10:
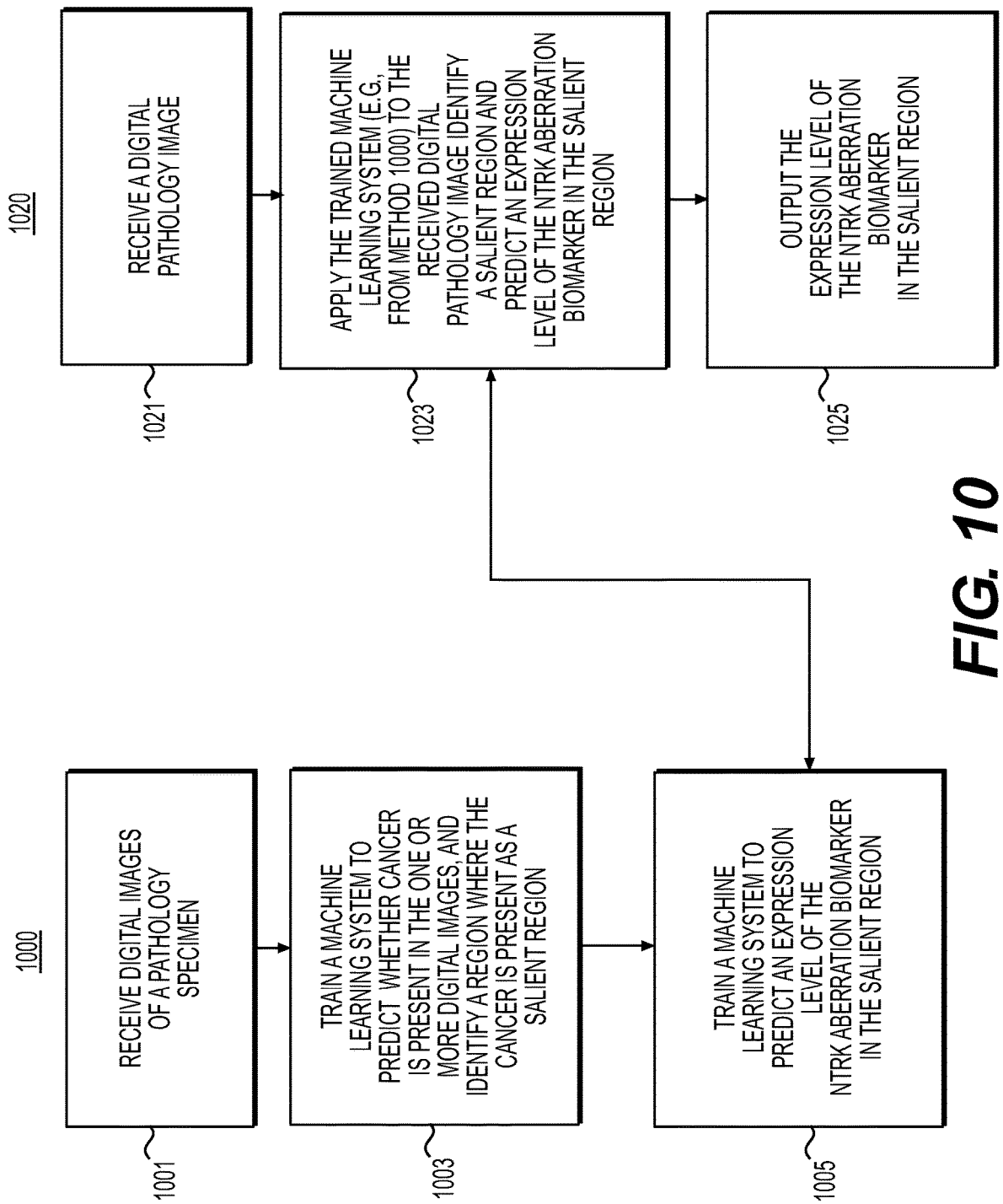
FIG. 10 is a flowchart illustrating an exemplary method for predicting neurotrophic receptor tyrosine kinase (NTRK) aberration biomarkers, according to an exemplary embodiment of the present disclosure.

As illustrated in FIG. 10, according to one embodiment, exemplary methods 1000 and 1020 for predicting neurotrophic receptor tyrosine kinase (NTRK) aberration biomarkers are described below.

Many cancers have NTRK aberrations, which may include fusion genes. These alterations may be found in a significant fraction of prostate, pancreas, breast, liver, lung, and/or skin cancers. NTRK fusions may be found in both pediatric and adult cancers. Specific drug treatments for patients whose tumors harbor fusion genes involving NTRK1, NTRK2 or NTRK3 have been approved. Fusion genes may be rare, and screening for these alterations may be onerous and immensely labor and/or time consuming. Techniques presented herein may be used to identify cancers harboring NTRK1, NTRK2 or NTRK3 fusion genes.

Exemplary methods 1000 and 1020 for predicting neurotrophic receptor tyrosine kinase (NTRK) aberration biomarkers may include one or more of the steps below. In step 1001, during a training phase, the method may include receiving one or more digital images of a tissue specimen stained with H&E into a digital storage device (e.g., hard drive, network drive, cloud storage, RAM, etc.), receiving, for one or more images, an indication of the presence or absence of the salient region, e.g., cancerous tissue, and/or receiving an indication of a tissue specimen type. One or more digital images may be broken into sub-regions and the saliency of one or more sub-regions may be determined. Regions may be specified in a variety of methods, including creating tiles of the image, segmentations based edge/contrast, segmentations via color differences, supervised determination by the machine learning system, and/or Edge-Boxes, etc.

In step 1003, the method may include training a machine learning algorithm that takes, as input, a digital image of a pathology specimen, and predicts whether a salient region exists, e.g., whether cancer is possibly present, using an AI-based method and/or manual specification. The machine learning algorithm may be performed in a weakly-supervised or strongly-supervised manner. The machine learning algorithm may be trained for a specific kind of cancer or it may be a pan-cancer model, enabling it to work for rare cancers in which an amount of training data is limited.

In step 1005, the method may include training the machine learning algorithm to predict an expression level of one or more of the NTRK aberration biomarkers based on the salient regions of the digital image of the pathology specimen and/or the received biomarker/score information. The method may include receiving an indication for each slide of the presence of an NTRK1, NTRK2 or NTRK3 fusion gene. The presence of the fusion may be indicated in a categorical scale (e.g., present vs absent). The indication may be assigned to the entire image and/or image sub-regions.

According to one embodiment, an exemplary method 1020 for using the biomarker tool to predict NTRK aberration biomarkers may include one or more of the steps below. In step 1021, the method may include receiving one or more digital images of a pathology specimen into a digital storage device (e.g., hard drive, network drive, cloud storage, RAM, etc.), and/or receiving an indication of a tissue specimen type. In step 1023, the method may include applying the salient region detector machine learning algorithm (e.g., method 1000 (e.g., deep neural network)) to the image to predict if cancer is possibly present in the received images and/or to identify salient image regions that may correspond to cancerous tissue using an AI-based method and/or manual specification. Additionally, the method may include applying the machine learning biomarker detection algorithm (e.g., method 1000) to the image to determine a prediction of a presence of an NTRK1, NTRK2 or NTRK3 fusion gene. The method may include assigning the presence of an NTRK1, NTRK2 or NTRK3 fusion gene to a diagnostic category.

In step 1025, the method may include outputting the prediction to an electronic storage device. The method may include displaying a visual indicator to alert the user (e.g., a pathologist, histology technician, etc.) of the expression levels of one or more biomarkers.

Figure 11:
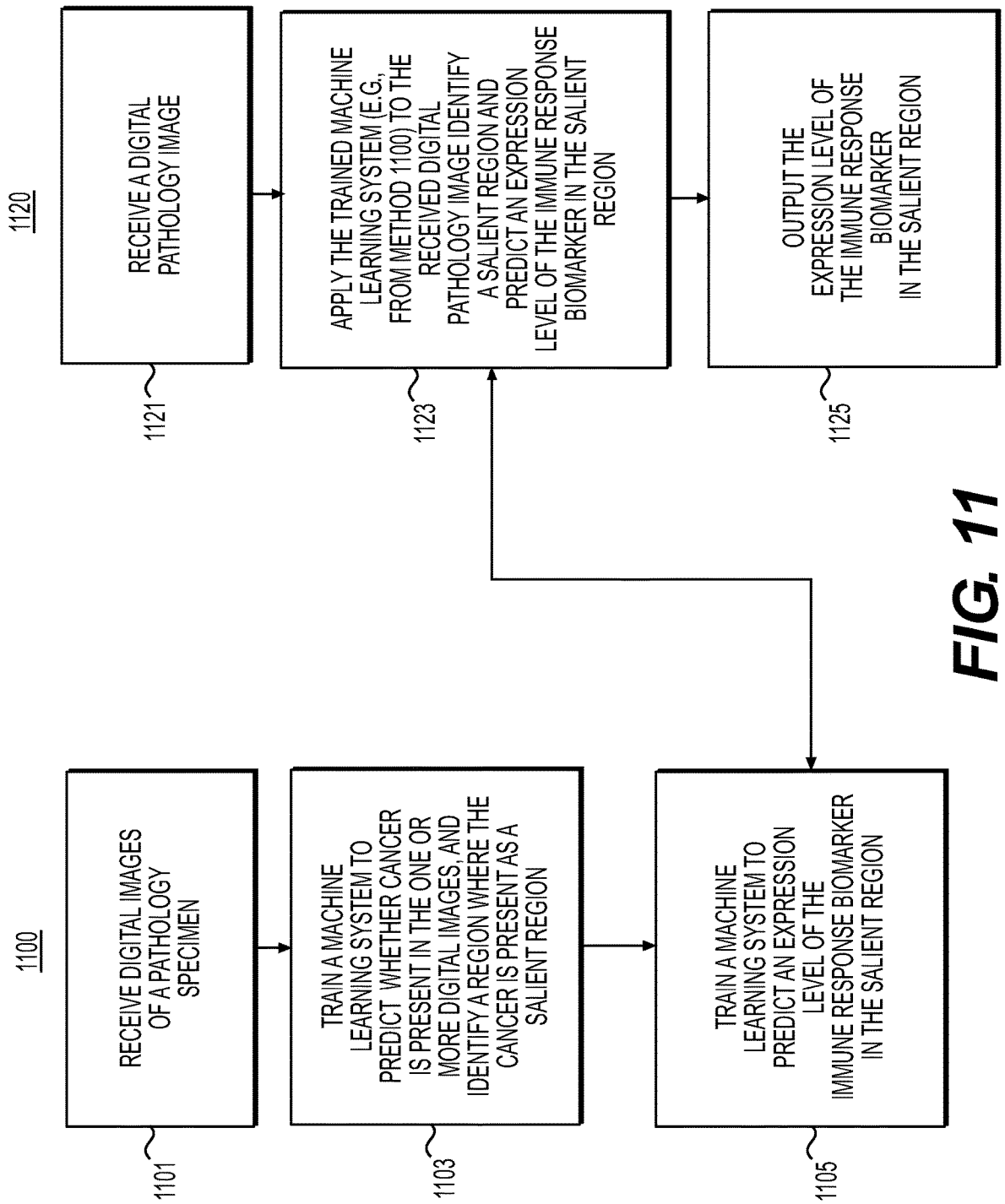
FIG. 11 is a flowchart illustrating an exemplary method for predicting immune response biomarkers, according to an exemplary embodiment of the present disclosure.

As illustrated in FIG. 11, according to one embodiment, exemplary methods 1100 and 1120 for predicting immune response biomarkers are described below.

Recognition of the tumor cell by the immune system for destruction may require a set of conditions that may be utilized in several biomarkers for assessment of a potential efficacy of immunotherapies including antibodies against PD1, PDL1, and/or CD28, among others. Some of these biomarkers may include a number of somatic mutations (e.g., tumor mutation burden), IHC for markers including PDL1 and/or PD1, gene expression signatures for the level of inflammation in the microenvironment, etc. Techniques presented herein may be used to identify cancers with potential to be recognized by the immune system and susceptible to checkpoint therapies.

Exemplary methods 1100 and 1120 for predicting immune response biomarkers may include one or more of the steps below. In step 1101, during a training phase, the method may include receiving one or more digital images of a tissue specimen stained with H&E into a digital storage device (e.g., hard drive, network drive, cloud storage, RAM, etc.), receiving, for one or more images, an indication of the presence or absence of the salient region, e.g., cancerous tissue, and/or receiving an indication of a tissue specimen type. One or more digital images may be broken into sub-regions and the saliency of one or more sub-regions may be determined. Regions may be specified in a variety of methods, including creating tiles of the image, segmentations based edge/contrast, segmentations via color differences, supervised determination by the machine learning system, and/or EdgeBoxes, etc.

In step 1103, the method may include training a machine learning algorithm that takes, as input, a digital image of a pathology specimen, and predicts whether a salient region exists, e.g., whether cancer is possibly present, using an AI-based method and/or manual specification. The machine learning algorithm may be performed in a weakly-supervised or strongly-supervised manner. The machine learning algorithm may be trained for a specific kind of cancer or it may be a pan-cancer model, enabling it to work for rare cancers in which an amount of training data is limited.

In step 1105, the method may include training the machine learning algorithm to predict an expression level of one or more of the immune response biomarkers based on the salient regions of the digital image of the pathology specimen and/or the received biomarker/score information. The method may include receiving an indication for each slide of the sensitivity to checkpoint inhibitor or tumor mutation burden or inflamed tumor microenvironment or PDL1/PD1 positivity. The presence of these may be indicated in a categorical scale (e.g., present vs absent). The indication may be assigned to the entire image and/or image sub-regions.

According to one embodiment, an exemplary method 1120 for using the biomarker tool to predict immune response biomarkers may include one or more of the steps below. In step 1121, the method may include receiving one or more digital images of a pathology specimen into a digital storage device (e.g., hard drive, network drive, cloud storage, RAM, etc.), and/or receiving an indication of a tissue specimen type. In step 1123, the method may include applying the salient region detector machine learning algorithm (e.g., method 1100 (e.g., deep neural network)) to the image to predict if cancer is possibly present in the received images and/or to identify salient image regions that may correspond to cancerous tissue using an AI-based method and/or manual specification. Additionally, the method may include applying the machine learning biomarker detection algorithm (e.g., method 1100) to the image to determine a prediction of a presence of immune response biomarkers. The method may include assigning the presence of immune response biomarkers to a diagnostic category.

In step 1125, the method may include outputting the prediction to an electronic storage device. The method may include displaying a visual indicator to alert the user (e.g., a pathologist, histology technician, etc.) of the expression levels of one or more biomarkers.

Figure 12:
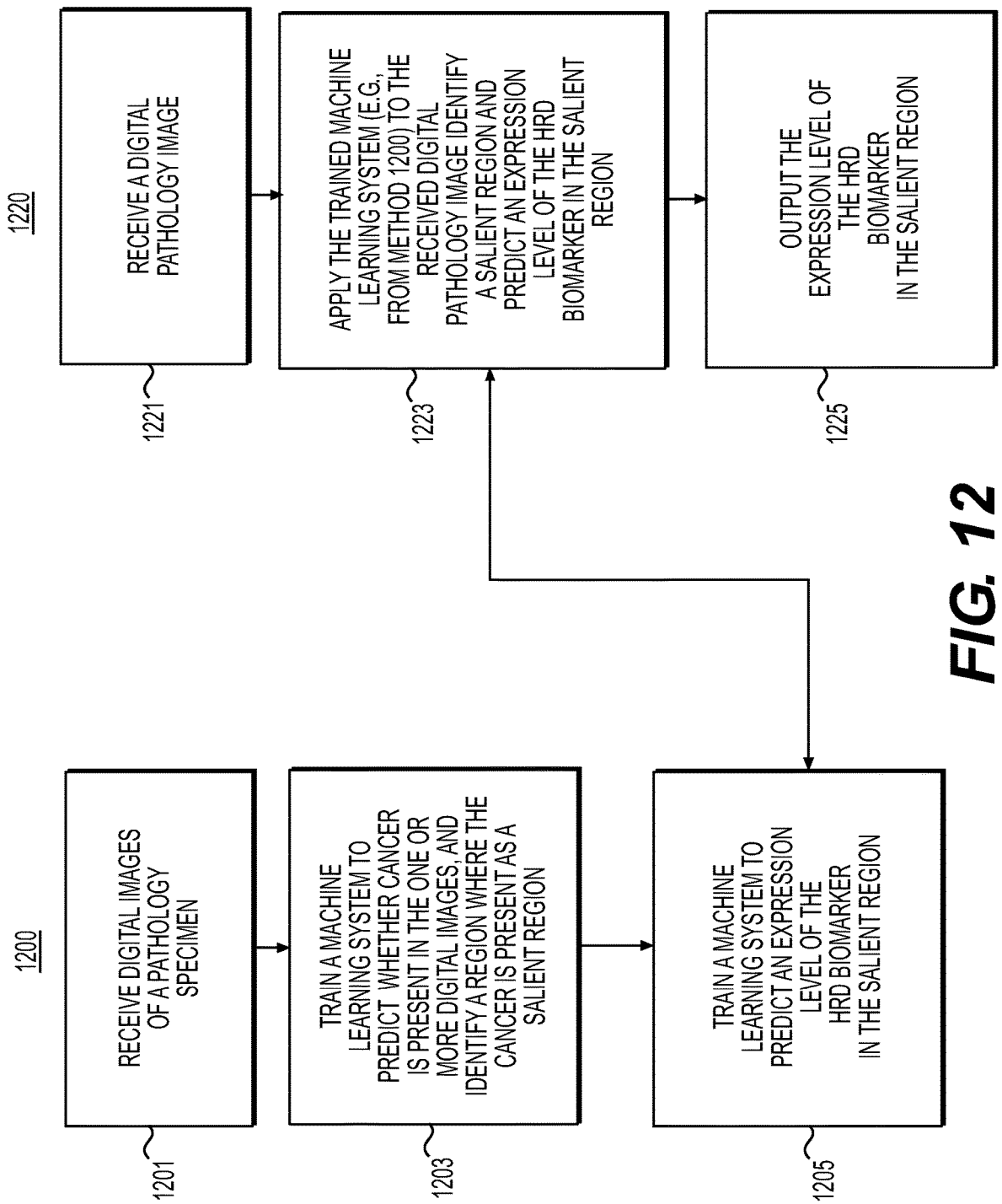
FIG. 12 is a flowchart illustrating an exemplary method for predicting homologous recombination DNA repair deficiency (HRD) biomarkers, according to an exemplary embodiment of the present disclosure.

As illustrated in FIG. 12, according to one embodiment, exemplary methods 1200 and 1220 for predicting homologous recombination DNA repair deficiency (HRD) biomarkers are described below.

Homologous recombination may be used by cells to fix harmful DNA breaks, especially double-strand breaks. HRD may be strongly associated with cancer, in particular breast, ovary, pancreatic and/or prostate cancer. Mutations affecting a homologous recombination DNA repair gene, such as BRCA1, BRCA2, PALB2, RAD51C and/or RAD51D, may increase the risk of breast, ovarian, pancreatic and/or prostate cancer development, but also may predict response to platinum-based chemotherapy and Poly (ADP) Ribose Polymerase (PARP) inhibitors. Sequencing analysis of constitutional DNA for the detection of mutations affecting homologous recombination DNA repair genes may be important for the use of PARP inhibitors in the care of patients with breast and/or ovarian cancer. In addition, sequencing analysis of tumor-derived DNA may provide evidence of HRD, as the lack of this specific modality of DNA repair may leave 'scars' in the genome.

Sequencing-based methods to identify HRD genomic scars may be available, but their clinical utility may be questionable. In addition, inactivation of some DNA repair genes, such as ATM and CHEK2, do not result in an HRD genomic scar, but may predict sensitivity to PARP inhibitors and/or other agents targeting specific DNA repair defects. Techniques presented herein may define the presence of inactivation of homologous recombination DNA repair-related genes, DNA damage response genes and/or HRD in human tumors based on the AI analysis of H&E stained sections. This embodiment may provide a biomarker for the use of PARP inhibitors and//or other agents that target tumors with HRD.

Exemplary methods 1200 and 1220 for predicting homologous recombination DNA repair deficiency (HRD) biomarkers may include one or more of the steps below. In step 1201, during a training phase, the method may include receiving one or more digital images of a tissue specimen stained with H&E into a digital storage device (e.g., hard drive, network drive, cloud storage, RAM, etc.), receiving, for one or more images, an indication of the presence or absence of the salient region, e.g., cancerous tissue, and/or receiving a tissue specimen type. One or more digital images may be broken into sub-regions and the saliency of one or more sub-regions may be determined. Regions may be specified in a variety of methods, including creating tiles of the image, segmentations based edge/contrast, segmentations via color differences, supervised determination by the machine learning system, and/or EdgeBoxes, etc.

In step 1203, the method may include training a machine learning algorithm that takes, as input, a digital image of a pathology specimen, and predicts whether a salient region exists, e.g., whether cancer is possibly present, based on the tissue specimen type, using an AI-based method and/or manual specification. The machine learning algorithm may be performed in a weakly-supervised or strongly-supervised manner.

In step 1205, the method may include training the machine learning algorithm to predict an expression level of one or more of the HRD biomarkers based on the salient regions of the digital image of the pathology specimen and/or the received biomarker/score information. The method may include receiving an indication of the presence of mutations (e.g., categorical) affecting homologous recombination and/or DNA damage response-related genes, whether these mutations are mono- or bi-allelic (e.g., categorical), and their variant allele (e.g., numerical) and cancer cell fractions (e.g., numerical). In addition, the presence (e.g., categorical) and abundance (e.g., numerical) for the HRD genomic scar may also be received. The indication may be assigned to the entire image and/or image sub-regions.

According to one embodiment, an exemplary method 1220 for using the biomarker tool to predict HRD biomarkers may include one or more of the steps below. In step 1221, the method may include receiving one or more digital images of a pathology specimen into a digital storage device (e.g., hard drive, network drive, cloud storage, RAM, etc.). In step 1223, the method may include applying the salient region detector machine learning algorithm (e.g., method 1200 (e.g., deep neural network)) to the image to predict if cancer is possibly present in the received images and/or to identify salient image regions that may correspond to cancerous tissue using an AI-based method and/or manual specification. Additionally, the method may include applying the machine learning biomarker detection algorithm (e.g., method 1200) to the image to determine a prediction of a presence of specific mutations, their variant allele fraction or cancer cell fraction, and HRD levels of the tumor. The method may include assigning a presence of specific mutations, their variant allele fraction or cancer cell fraction, and HRD levels of the tumor to a diagnostic category.

In step 1225, the method may include outputting the prediction to an electronic storage device. The method may include displaying a visual indicator to alert the user (e.g., a pathologist, histology technician, etc.) of the expression levels of one or more biomarkers.

Figure 13:
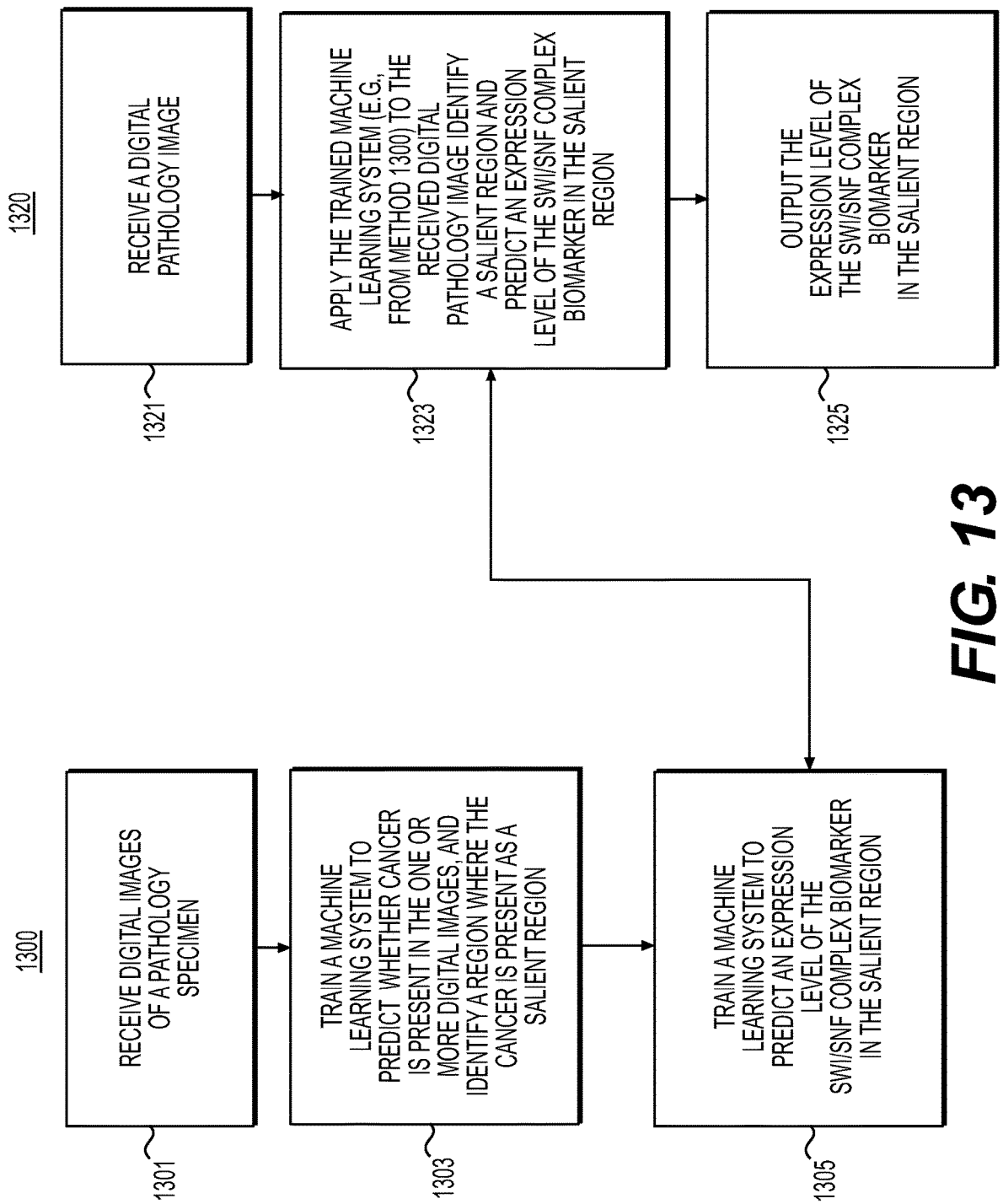
FIG. 13 is a flowchart illustrating an exemplary method for predicting SWItch/Sucrose Non-Fermentable (SWI/SNF) biomarkers, according to an exemplary embodiment of the present disclosure.

As illustrated in FIG. 13, according to one embodiment, exemplary methods 1300 and 1320 for predicting SWItch/Sucrose Non-Fermentable (SWI/SNF) biomarkers are described below.

SWI/SNF is a group of proteins that remodel how DNA is packaged. The SWI/SNF complex may function as a tumor suppressor, and SWI/SNF proteins may be absent in cancerous tissue. Alterations in the genes of the SWI/SNF complex may cause resistance to endocrine therapy in patients with ER-positive breast cancers. Techniques presented herein may predict a presence or absence of SWI/SNF subunits from digital images of pathological specimens.

Exemplary methods 1300 and 1320 for predicting SWI/SNF biomarkers may include one or more of the steps below. In step 1301, during a training phase, the method may include receiving one or more digital images of a tissue specimen stained with H&E into a digital storage device (e.g., hard drive, network drive, cloud storage, RAM, etc.), receiving, for one or more images, an indication of the presence or absence of the salient region, e.g., cancerous tissue, and/or receiving an indication of a tissue specimen type. One or more digital images may be broken into sub-regions and the saliency of one or more sub-regions may be determined. Regions may be specified in a variety of methods, including creating tiles of the image, segmentations based edge/contrast, segmentations via color differences, supervised determination by the machine learning system, and/or EdgeBoxes, etc.

In step 1303, the method may include training a machine learning algorithm that takes, as input, a digital image of a pathology specimen, and predicts whether a salient region exists, e.g., whether cancer is possibly present, based on the indications, using an AI-based method and/or manual specification. The machine learning algorithm may be performed in a weakly-supervised or strongly-supervised manner.

In step 1305, the method may include training the machine learning algorithm to predict an expression level of one or more of the SWI/SNF complex biomarkers based on the salient regions of the digital image of the pathology specimen and/or the received biomarker/score information. The method may include receiving an indication of a presence of mutations (e.g., categorical) affecting genes of the SWI/SNF complex, whether these mutations are mono- or bi-allelic (e.g., categorical), and their variant allele (e.g., numerical) and cancer cell fractions (e.g., numerical). The indication may be assigned to the entire image and/or image sub-regions.

According to one embodiment, an exemplary method 1320 for using the biomarker tool to predict SWI/SNF complex biomarkers may include one or more of the steps below. In step 1321, the method may include receiving one or more digital images of a pathology specimen into a digital storage device (e.g., hard drive, network drive, cloud storage, RAM, etc.). In step 1323, the method may include applying the salient region detector machine learning algorithm (e.g., method 1300 (e.g., deep neural network)) to the image to predict if cancer is possibly present in the received images and/or to identify salient image regions that may correspond to cancerous tissue using an AI-based method and/or manual specification. Additionally, the method may include applying the machine learning biomarker detection algorithm (e.g., method 1300) to the image to determine a prediction of a presence of mutations affecting genes of the SWI/SNF complex, whether these mutations are mono- or bi-allelic, and their variant allele and cancer cell fractions. The method may include assigning the presence of mutations affecting genes of the SWI/SNF complex, whether these mutations are mono- or bi-allelic, and their variant allele and cancer cell fractions to a diagnostic category.

In step 1325, the method may include outputting the prediction to an electronic storage device. The method may include displaying a visual indicator to alert the user (e.g., a pathologist, histology technician, etc.) of the expression levels of one or more biomarkers.

Figure 14:
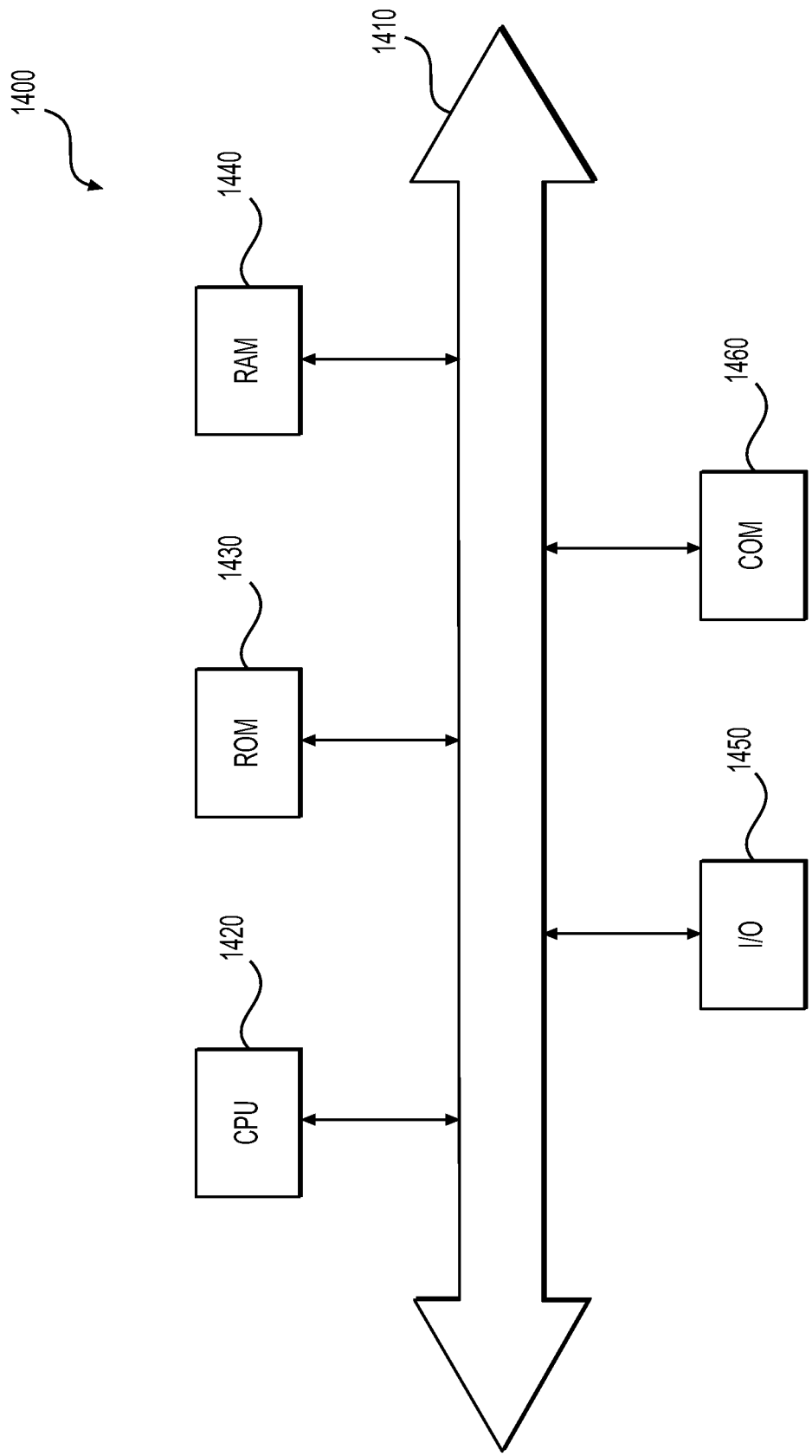
FIG. 14 depicts an example system that may execute techniques presented herein.

As shown in FIG. 14, device 1400 may include a central processing unit (CPU) 1420. CPU 1420 may be any type of processor device including, for example, any type of special purpose or a general-purpose microprocessor device. As will be appreciated by persons skilled in the relevant art, CPU 1420 also may be a single processor in a multi-core/multi-processor system, such system operating alone, or in a cluster of computing devices operating in a cluster or server farm. CPU 1420 may be connected to a data communication infrastructure 1410, for example, a bus, message queue, network, or multi-core message-passing scheme.

Device 1400 also may include a main memory 1440, for example, random access memory (RAM), and also may include a secondary memory 1430. Secondary memory 1430, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 1430 may include other similar means for allowing computer programs or other instructions to be loaded into device 1400. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 1400.

Device 1400 also may include a communications interface ("COM") 1460. Communications interface 1460 allows software and data to be transferred between device 1400 and external devices. Communications interface 1460 may include a modem, a network interface (such as an Ethernet card), a communications port, a PCMCIA slot and card, or the like. Software and data transferred via communications interface 1460 may be in the form of signals, which may be electronic, electromagnetic, optical, or other signals capable of being received by communications interface 1460. These signals may be provided to communications interface 1460 via a communications path of device 1400, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 1400 also may include input and output ports 1450 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and modules may be implemented in software, hardware, or a combination of software and hardware.

The tools, modules, and functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples be considered as exemplary only.

What is claimed is:

1. A computer-implemented method for analyzing an image corresponding to a specimen, the method comprising:
  receiving a target electronic image corresponding to a target specimen, the target specimen comprising a tissue sample of a patient;
  applying a first machine learning algorithm to the target electronic image to identify one or more salient regions of the target electronic image;
  applying a second machine learning algorithm focusing on the one or more salient regions of the target electronic image to identify a region of interest of the target specimen and determine a numeric expression level of, category of, and a numeric probability that there is a presence of a biomarker in the region of interest of the target specimen, the biomarker comprising at least one from among an epithelial growth factor receptor (EGFR) biomarker and/or a DNA mismatch repair (MMR) deficiency biomarker, the second machine learning algorithm having been generated by processing a plurality of training images to predict whether a region of interest is present in the target electronic image, the training images comprising images of human tissue and/or images that are algorithmically generated; wherein determining the numeric expression level of the biomarker includes:
    breaking the one or more salient regions of target electronic image into a plurality of tiles;
    determining, by the second machine learning algorithm, the numeric expression level corresponding to a prediction for each tile to determine a plurality of tile predictions; and
    aggregating the plurality of tile predictions into at least one part level numeric expression level prediction for sub-regions of the one or more salient regions, wherein the at least one part level numeric expression level prediction and prediction for each tile are fed into the second machine learning algorithm to determine the numeric expression level prediction; and
  outputting the determined numeric expression level of, category of, and presence of the biomarker in the region of interest.

2. The computer-implemented method of claim 1, wherein the identifying the region of interest of the target specimen comprises determining whether a region of interest is present in any of the plurality of tiles.

3. The computer-implemented method of claim 1, wherein the identifying the region of interest of the target specimen comprises:
  segmenting the target electronic image based on edge and/or contrast, segmenting the target electronic image using color differences, and/or supervised determination; and determining whether a region of interest is present in any of the plurality of tiles.

4. The computer-implemented method of claim 1, further comprising:
determining numeric expression level of, a biomarker in a region of interest by determining a first expression score for each tile of the target electronic image, and aggregating the first expression score for each of the tiles to determine a second expression score for part of the target specimen.

5. The computer-implemented method of claim 1, wherein the determining of the category of a biomarker in the region of interest comprises:
grouping numeric expression levels into one or more diagnostic categories, the one or more diagnostic categories representing a scale of a presence of the biomarker in the region of interest; and
identifying a diagnostic category, among the one or more diagnostic categories, to classify the biomarker in the region of interest.

6. The computer-implemented method of claim 1, wherein the outputting the determined numeric expression level of, category of, and presence of the biomarker in the region of interest comprises displaying a visual indicator for the numeric expression level of, category of, and/or presence of the biomarker, and displaying one or more treatment options based on the numeric expression level of, category of, and presence of the biomarker.

7. The computer-implemented method of claim 1, further comprising:
notifying an external user of the presence or absence of the biomarker in the region of interest.

8. The method of claim 1, further including:
determining, based on the determined numeric expression level of, category of, and presence of the biomarker, one or more treatment recommendations for the patient.

9. The method of claim 1, wherein applying a first machine learning algorithm to the target electronic image to identify one or more salient regions of the target electronic image further includes:
using machine learning visualization tools to create a detailed heatmap; and
extracting the salient regions from the heatmap.

10. A system for analyzing an image corresponding to a specimen, the system comprising:
at least one memory storing instructions; and
at least one processor configured to execute the instructions to perform operations comprising:
receiving a target electronic image corresponding to a target specimen, the target specimen comprising a tissue sample of a patient;
applying a first machine learning algorithm to the target electronic image to identify one or more salient regions of the target electronic image;
applying a second machine learning algorithm focusing on the one or more salient regions of the target electronic image to identify a region of interest of the target specimen and determine a numeric expression level of, category of, and a numeric probability that there is a presence of a biomarker in the region of interest of the target specimen, the biomarker comprising at least one from among an epithelial growth factor receptor (EGFR) biomarker and/or a DNA mismatch repair (MMR) deficiency biomarker, the second machine learning algorithm having been generated by processing a plurality of training images to predict whether a region of interest is present in the target electronic image, the training images comprising images of human tissue and/or images that are algorithmically generated; wherein determining the numeric expression level of the biomarker includes:
breaking the one or more salient regions of target electronic image into a plurality of tiles;
determining, by the second machine learning algorithm, the numeric expression level corresponding to a prediction for each tile to determine a plurality of tile predictions; and
aggregating the plurality of tile predictions into at least one part level numeric expression level prediction for sub-regions of the one or more salient regions, wherein the at least one part level numeric expression level prediction and prediction for each tile are fed into the second machine learning algorithm to determine the numeric expression level prediction; and
outputting the determined numeric expression level of, category of, and presence of the biomarker in the region of interest.

11. The system of claim 10, wherein the identifying the region of interest of the target specimen comprises determining whether a region of interest is present in any of the plurality of tiles.

12. The system of claim 10, wherein the identifying the region of interest of the target specimen comprises:
segmenting the target electronic image based on edge and/or contrast, segmenting the target electronic image using color differences, and/or supervised determination; and
determining whether a region of interest is present in any of the plurality of tiles.

13. The system of claim 10, further comprising:
determining a numeric expression level of, a biomarker in a region of interest by determining a first expression score for each tile of the target electronic image, and aggregating the first expression score for each of the tiles to determine a second expression score for part of the target specimen.

14. The system of claim 10, wherein the determining of the category of the biomarker in the region of interest comprises:
grouping numeric expression levels into one or more diagnostic categories, the one or more diagnostic categories representing a scale of a presence of the biomarker in the region of interest; and
identifying a diagnostic category, among the one or more diagnostic categories, to classify the biomarker in the region of interest.

15. The system of claim 10, wherein the outputting the determined numeric expression level of, category of, and presence of the biomarker in the region of interest comprises displaying a visual indicator for the numeric expression level of, category of, and/or presence of the biomarker, and displaying one or more treatment options based on the numeric expression level of, category of, and presence of the biomarker.

16. A non-transitory computer-readable medium storing instructions that, when executed by processor, cause the processor to perform a method for analyzing an image corresponding to a specimen, the method comprising:
receiving a target electronic image corresponding to a target specimen, the target specimen comprising a tissue sample of a patient;

applying a first machine learning algorithm to the target electronic image to identify one or more salient regions of the target electronic image;

applying a second machine learning algorithm focusing on the one or more salient regions of the target electronic image to identify a region of interest of the target specimen and determine a numeric expression level of, category of, and a numeric probability that there is a presence of a biomarker in the region of interest of the target specimen, the biomarker comprising at least one from among an epithelial growth factor receptor (EGFR) biomarker and/or a DNA mismatch repair (MMR) deficiency biomarker, the second machine learning algorithm having been generated by processing a plurality of training images to predict whether a region of interest is present in the target electronic image, the training images comprising images of human tissue and/or images that are algorithmically generated; wherein determining the numeric expression level of the biomarker includes:

breaking the one or more salient regions of target electronic image into a plurality of tiles;

determining, by the second machine learning algorithm, the numeric expression level corresponding to a prediction for each tile to determine a plurality of tile predictions; and aggregating the plurality of tile predictions into at least one part level numeric expression level prediction for sub-regions of the one or more salient regions, wherein the at least one part level numeric expression level prediction and prediction for each tile are fed into the second machine learning algorithm to determine the numeric expression level prediction; and outputting the determined numeric expression level of, category of, and presence of the biomarker in the region of interest.

17. The non-transitory computer-readable medium of claim 16, wherein the identifying the region of interest of the target specimen comprises determining whether a region of interest is present in any of the plurality of tiles.

18. The non-transitory computer-readable medium of claim 16, wherein the identifying the region of interest of the target specimen comprises:

segmenting the target electronic image based on edge and/or contrast, segmenting the target electronic image using color differences, and/or supervised determination; and determining whether a region of interest is present in any of the plurality of tiles.

19. The non-transitory computer-readable medium of claim 16, further comprising:

determining numeric expression level of a biomarker in a region of interest by determining a first expression score for each tile of the target electronic image, and aggregating the first expression score for each of the tiles to determine a second expression score for part of the target specimen.

20. The non-transitory computer-readable medium of claim 16, wherein the determining of the category of a biomarker in the region of interest comprises:

grouping numeric expression levels into one or more diagnostic categories, the one or more diagnostic categories representing a scale of a presence of the biomarker in the region of interest; and identifying a diagnostic category, among the one or more diagnostic categories, to classify the biomarker in the region of interest.

* * * * *